US012330107B2

(12) United States Patent
Hourani et al.

(10) Patent No.: US 12,330,107 B2
(45) Date of Patent: *Jun. 17, 2025

(54) PURIFICATION DEVICE HAVING HEATED FILTER FOR KILLING BIOLOGICAL SPECIES, INCLUDING COVID-19

(71) Applicants: Integrated Viral Protection Solutions, LLC, Houston, TX (US); University of Houston System, Houston, TX (US)

(72) Inventors: Monzer A. Hourani, Houston, TX (US); Zhifeng Ren, Houston, TX (US); Luo Yu, Houston, TX (US)

(73) Assignee: University of Houston System, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/883,977

(22) Filed: May 26, 2020

(65) Prior Publication Data

US 2021/0339183 A1 Nov. 4, 2021

Related U.S. Application Data

(60) Provisional application No. 63/018,442, filed on Apr. 30, 2020, provisional application No. 63/018,448, filed on Apr. 30, 2020.

(51) Int. Cl.
*B01D 46/00* (2022.01)
*A61L 9/20* (2006.01)
(Continued)

(52) U.S. Cl.
CPC ............ *B01D 46/4263* (2013.01); *A61L 9/20* (2013.01); *B01D 39/2027* (2013.01);
(Continued)

(58) Field of Classification Search
CPC .......... B01D 46/4263; B01D 46/448; B01D 46/444; B01D 46/0028; B01D 46/4245;
(Continued)

(56) References Cited

U.S. PATENT DOCUMENTS 2,594,101 A  7/1950  Volker
2,849,589 A  8/1958  Lancaster
(Continued)

FOREIGN PATENT DOCUMENTS

CN  101929255 A  12/2010
CN  103002606 A  3/2013
(Continued)

OTHER PUBLICATIONS

First Examination Report in counterpart GCC Appl. 2020-40143, dated Aug. 31, 2021, 4-pgs.
(Continued)

*Primary Examiner* — Robert Clemente
(74) *Attorney, Agent, or Firm* — Blank Rome LLP

(57) ABSTRACT

An apparatus is used with supplied power for treating air flow of an air handing system of a facility. A frame has a plenum with an inlet and an outlet. The frame is configured to position in the air flow of the air handing system for passage of the air flow therethrough. A filter is disposed in the plenum and is configured to filter the air flow therethrough up to a filtration threshold. An ultraviolet light source disposed in the plenum is connected in electrical communication with the supplied power and is configured to generate ultraviolet radiation in the plenum. A permeable metal barrier disposed in the plenum is configured to impede the air flow therethrough up to an impedance threshold. The barrier is connected in electrical communication to the supplied power and is heated to a surface temperature.

33 Claims, 15 Drawing Sheets

(51) Int. Cl.
*B01D 39/20* (2006.01)
*B01D 46/42* (2006.01)
*B01D 46/44* (2006.01)
*B60H 3/06* (2006.01)
*F24F 8/10* (2021.01)
*F24F 8/22* (2021.01)

(52) U.S. Cl.
CPC ..... *B01D 46/0028* (2013.01); *B01D 46/4245* (2013.01); *B01D 46/429* (2013.01); *B01D 46/444* (2013.01); *B01D 46/448* (2013.01); *B60H 3/0608* (2013.01); *F24F 8/10* (2021.01); *A61L 2209/11* (2013.01); *A61L 2209/111* (2013.01); *A61L 2209/12* (2013.01); *A61L 2209/14* (2013.01); *A61L 2209/15* (2013.01); *B01D 2279/50* (2013.01); *B01D 2279/65* (2013.01); *F24F 8/22* (2021.01); *F24F 2221/125* (2013.01); *F24F 2221/34* (2013.01)

(58) Field of Classification Search
CPC ............ B01D 39/2027; B01D 2279/50; B01D 2279/65; B60H 3/0608; F24F 3/1603; F24F 2003/1667; F24F 2221/34; A61L 9/20; A61L 2209/11; A61L 2209/15
USPC .............. 55/385.2, 385.1, DIG. 34; 454/187; 422/121, 186.04, 186.3
See application file for complete search history.

(56) References Cited

U.S. PATENT DOCUMENTS

| | | | |
|---|---|---|---|
| 3,395,972 A | 8/1968 | Hardison | |
| 4,661,126 A | 4/1987 | Inagani et al. | |
| 4,707,167 A * | 11/1987 | Saito | B01D 46/523 55/385.2 |
| 5,180,409 A | 1/1993 | Fischer | |
| 5,192,346 A | 3/1993 | Kowalczyk | |
| 5,837,207 A * | 11/1998 | Summers | A61L 9/20 422/121 |
| 6,464,760 B1 | 10/2002 | Sham et al. | |
| 6,500,387 B1 * | 12/2002 | Bigelow | A61L 9/20 250/432 R |
| 6,680,028 B1 | 1/2004 | Harris | |
| 6,716,406 B2 * | 4/2004 | Reisfeld | A61L 9/20 423/245.1 |
| 7,083,663 B2 | 8/2006 | Shih et al. | |
| 7,270,591 B2 | 9/2007 | Deshpande et al. | |
| 7,625,277 B2 * | 12/2009 | Palmer | F24F 11/77 454/238 |
| 8,263,012 B2 * | 9/2012 | Hay | F24F 8/30 422/186.04 |
| 8,444,747 B2 * | 5/2013 | Kristensson | F24F 5/0042 128/202.13 |
| 8,529,830 B2 | 9/2013 | Zhou et al. | |
| 8,772,744 B1 | 7/2014 | Liu | |
| 10,117,961 B2 | 11/2018 | Horne et al. | |
| 10,471,170 B2 * | 11/2019 | Lee | B01J 23/866 |
| 11,446,600 B2 | 9/2022 | Hourani | |
| 2004/0003581 A1 | 1/2004 | Lim | |
| 2004/0041564 A1 | 3/2004 | Brown | |
| 2004/0047776 A1 | 3/2004 | Thomsen | |
| 2005/0092181 A1 * | 5/2005 | Shih | H05B 3/12 55/490.1 |
| 2008/0031783 A1 | 2/2008 | Briggs et al. | |
| 2008/0086994 A1 * | 4/2008 | Descotes | F24F 1/005 55/471 |
| 2008/0121823 A1 * | 5/2008 | Goel | A61L 9/20 250/504 R |
| 2010/0032055 A1 | 2/2010 | Sangi | |
| 2010/0323603 A1 | 12/2010 | Lans | |
| 2011/0308522 A1 | 12/2011 | Kimm | |
| 2012/0192717 A1 | 8/2012 | Gonze | |
| 2012/0196147 A1 | 8/2012 | Rabiei | |
| 2013/0256631 A1 | 10/2013 | Khan et al. | |
| 2013/0294968 A1 | 11/2013 | Owen et al. | |
| 2014/0369894 A1 * | 12/2014 | Hingorani | F24F 8/167 29/458 |
| 2015/0092181 A1 * | 4/2015 | Nishita | G01C 1/04 356/4.01 |
| 2015/0359921 A1 * | 12/2015 | Palmer | A61L 9/20 422/4 |
| 2016/0067647 A1 | 3/2016 | Tate | |
| 2017/0028820 A1 | 2/2017 | Walsh | |
| 2017/0139386 A1 | 5/2017 | Pillai et al. | |
| 2017/0292797 A1 | 10/2017 | Roberge | |
| 2018/0050124 A1 | 2/2018 | Lee | |
| 2019/0063763 A1 * | 2/2019 | Kleinberger | A61L 2/022 |
| 2019/0083673 A1 * | 3/2019 | Munn | A61L 2/10 |
| 2020/0009286 A1 * | 1/2020 | Zarcone | F21S 9/022 |
| 2020/0086257 A1 | 3/2020 | Liu | |
| 2020/0182496 A1 | 6/2020 | Xiao et al. | |
| 2020/0300460 A1 | 9/2020 | Rush | |
| 2021/0339183 A1 | 11/2021 | Hourani | |
| 2021/0339184 A1 | 11/2021 | Hourani | |
| 2023/0119976 A1 * | 4/2023 | Maletich | F24F 8/158 55/307 |

FOREIGN PATENT DOCUMENTS

| | | |
|---|---|---|
| CN | 203731560 U | 7/2014 |
| CN | 204404388 U | 6/2015 |
| CN | 204478279 U | 7/2015 |
| CN | 205593084 U | 9/2016 |
| CN | 206919206 U | 1/2018 |
| CN | 206973703 U | 2/2018 |
| CN | 206973773 U | 2/2018 |
| CN | 108779925 A | 11/2018 |
| CN | 108981014 A | 12/2018 |
| CN | 209524549 U | 10/2019 |
| CN | 111043670 A | 4/2020 |
| CN | 112325461 A | 2/2021 |
| JP | S47044891 | 11/1972 |
| JP | 50128324 | 4/1974 |
| JP | 60193517 | 10/1985 |
| JP | 61171514 A | 8/1986 |
| JP | 01210010 A | 8/1989 |
| JP | H09126551 A | 5/1997 |
| JP | 2004508163 A | 3/2004 |
| JP | 2004130173 A | 4/2004 |
| JP | 2005013687 A | 1/2005 |
| JP | 2005137871 A | 6/2005 |
| JP | 2007-44432 A | 2/2007 |
| JP | 2011224121 A | 11/2011 |
| JP | 2015104400 A | 6/2015 |
| JP | 6019351 B2 | 11/2016 |
| JP | 2018509499 A | 4/2018 |
| KR | 20100036438 A | 4/2010 |
| KR | 20170035481 A | 3/2017 |
| KR | 20180003833 A | 1/2018 |
| WO | 200220064 A2 | 3/2002 |
| WO | 2004006969 A1 | 1/2004 |
| WO | 2005075000 A1 | 8/2005 |
| WO | 2005124241 A1 | 12/2005 |
| WO | 2016135257 A2 | 9/2016 |
| WO | 2019056323 A1 | 3/2019 |
| WO | 2019204570 A1 | 10/2019 |
| WO | 2021221698 A1 | 11/2021 |
| WO | 2021221699 A1 | 11/2021 |

OTHER PUBLICATIONS

First Examination Report in counterpart GCC Appl. 2020-40144, dated Aug. 31, 2021, 4-pgs.
Brown, "This Portable furnace could stop coronavirus in its track" dated Mar. 18, 2020.
International Search Report and Written Opinion in PCT Appl. PCT/US20/35608, dated Oct. 20, 2020.

(56) References Cited

OTHER PUBLICATIONS

First Office Action in counterpart Chinese Appl. 202010849987.X, dated Jul. 29, 2021, 6-pgs.

First Office Action in counterpart Chinese Appl. 202010849059.3, dated Jul. 29, 2021, 6-pgs.

First Office Action in counterpart Japanese Appl. 2020-129200, dated Jun. 8, 2021.

First Office Action in counterpart Japanese Appl. 2020-129203, dated May 11, 2021.

Notice of Reasons for Refusal in counterpart JP Appl. 2020-129203, dated Jan. 11, 2022, 11-pgs.

Search Report and Written Opinion in counterpart Singapore Appl. 10202007442S, dated Sep. 10, 2021, 11-pgs.

Search Report and Written Opinion in counterpart Singapore Appl. 10202007444V, dated Jan. 20, 2022, 10-pgs.

High-Performance Alloys for Resistance to Aqueous Corrosion, 2001, obtained from URL at https://www.parrinst.com/wpcontent/uploads/downloads/2011/07/Parr_Inconel-Incoloy-Monel-Nickel-Corrosion-Info.pdf.

Yu, L. et al., "Catching and killing of airborne SARS-COV-2 to control spread of COVID-19 by a heated air disinfection system," Materials Today Physics, 15 (2020) 100249, Jul. 7, 2020, 5-pgs.

International Search Report and Written Opinion Corresponding to Application No. PCT/US2021/062204, dated Jan. 11, 2022.

Office Action in U.S. Appl. No. 17/118,379, dated Apr. 7, 2021, 8-pgs.

Final Office Action in U.S. Appl. No. 17/118,379, dated Jul. 20, 2021, 9-pgs.

International Search Report dated Sep. 8, 2020 issued in counterpart PCT Application No. PCT/US2020/035607.

Extended European Search Report issued Dec. 6, 2023 in counterpart European Patent Application No. 20933580.1 (10 pages).

Office Action issued Feb. 26, 2024 in corresponding U.S. Appl. No. 18/231,644 (10 pages).

Office Action issued Mar. 28, 2024 in corresponding U.S. Appl. No. 17/889,596 (11 pages).

Office action issued Sep. 26, 2024 in Mexican Patent Application No. MX/A/2020/009035, 6 pages.

Decision to Grant issued Mar. 5, 2025 in counterpart Japanese Application No. 2022-566444 (with translation). 6 pages.

Decision to Grant issued Mar. 5, 2025 in counterpart Japanese Application No. 2022-566443 (with translation). 6 pages.

* cited by examiner

PURIFICATION DEVICE HAVING HEATED FILTER FOR KILLING BIOLOGICAL SPECIES, INCLUDING COVID-19

CROSS-REFERENCE TO RELATED APPLICATIONS

This application claims priority to U.S. Provisional Appl. Nos. 63/018,442 and 63/018,448 both filed 30 Apr. 2020, which are incorporated herein by reference. This application is filed concurrently with U.S. Appl. Ser. No. 16/883,981, entitled "Mobile Purification Device Having Heated Filter for Killing Biological Species, Including COVID-19", which is incorporated herein by reference in its entirety.

BACKGROUND OF THE DISCLOSURE

Various infectious pathogens, including bacterium, viruses, and other microorganism can cause disease in humans. The deadly Human SARS-CoV-2 strain (COVID-19) pandemic has impacted the human condition at all levels of life as we know it around the globe. The COVID-19 infection is persistently spread by circulating air flow as the primary mechanism for transmission. There are few active strategies to protect the public against COVID-19, and current strategies are widely debated, costly, and inefficient. A passive approach to condition and purify circulating air in all environments is needed to combat aerosolized COVID-19 immediately because current filter and air-purification technologies are not successful at killing the small sized (0.05-0.2 microns) COVID-19 virus.

Overall, air filtration is used in heating, ventilating, and air conditioning (HVAC) systems to remove dust, pollen, mold, particulates, and the like from the air being moved through a facility by the system. The filters used for the filtration can come in a number of forms and can be configured to filter particles of a given size with a given efficiency.

For example, high-efficiency particulate air (HEPA) filters are commonly used in cleanrooms, operating rooms, pharmacies, homes, etc. These filters can be made of different types of media, such as fiberglass media, ePTFE media, etc., and may have activated carbon-based material. In general, HEPA filters can filter over 99 percent of particles with a diameter of a given size (e.g., 0.3 microns or larger in size). Even with their efficiency, HEPA filters may not stop pathogens (virions, bacteria, etc.) of very small size.

Ultraviolet (UV) germicidal lights can stop pathogens, such as bacteria, viruses, and mold. The UV germicidal lights produce ultraviolet radiation, which can then damage the genetic material of the microorganisms. The damage may kill the pathogen or make them unable to reproduce. Extended exposure to the UV radiation can also break down pathogens that have deposited on an irradiated surface.

One example of an ultraviolet system includes an upper room air ultraviolet germicidal irradiation (UVGI) system. In the UVGI system, the UV germicidal light is installed near the ceiling in an occupied room. Air circulated by convection near the ceiling in the upper portion of the space is then irradiated within an active field of the UV germicidal light. UVGI systems can also be installed in the ducts of HVAC systems and can irradiate the small airborne particles containing microorganisms as the air flows through the ducts.

Although existing systems for filtration and germicidal irradiation can be effective in treating air to remove particulates and damage pathogens, there is a continuing need to purify air in populated environs, such as facilities, homes, workspaces, hospitals, nursing homes, sporting venues, and the like, to reduce the spread of pathogens, such as bacteria, viruses, and molds, even more.

In particular, the 2019 novel coronavirus disease (COVID-19) is a new virus of global health significance caused by infection of severe acute respiratory syndrome coronavirus 2 (SARS-CoV-2). COVID-19 is thought to spread from person to person in close contact through respiratory droplets. Studies show the virus can survive for hours at a time and can be persistently carried by airflow. For this reason, it is believed that a stationary 6-feet separation is ineffective in a situation where people spend a long time together in a room because infection can simply be carried by the airflow.

For example, COVID-19 (Sars-CoV-2) may survive in droplets for up to three hours after being coughed in the air, and convection in the air is thought to be the primary mechanism for the spread of the infection. Accordingly, droplet-spray and convection can drive direct airborne infection, and social distancing can be ineffective for enclosed environments were people spend a long time together.

As there is no current cure for COVID-19, environmental purification strategies can help slow the spread of the virus. Unfortunately, current systems to treat circulated air are expensive and use primarily UV germicidal light. These products require professional installation, are not accessible to the general public per se, and have not been used to kill COVID-19. Moreover, filtration in an HVAC system can be ineffective. COVID-19 measures between 0.05 to 0.2 microns, but HEPA filters can filter particulate larger than 0.3 microns so additional protection is needed against the spread of COVID-19.

For these reasons, the subject matter of the present disclosure is directed to overcoming, or at least reducing the effects of, one or more of the problems set forth above.

SUMMARY OF THE DISCLOSURE

The subject matter of the present disclosure is directed to a purification device that filters air and seeks to destroy viruses, bacteria, mold, pollens, volatile organic compounds, allergens, and pollutants. The purification device is intended to be affordable, easily installed, accessible and useable in both residential and commercial settings. The purification device can be applied to real world solutions to best reduce viruses, such as COVID-19, and other pathogens in the circulating air, and the purification device can be deployed as a specialized heated filter for use in commercial, residential, mass transit, and public venues.

For example and as discussed below, the purification device includes a barrier heater or heated filter that uses targeted thermal conduction of high efficiency nickel foam/mesh raised to temperatures proven to kill pathogens, such as corona viruses (such as COVID-19). The purification device also includes an ultraviolet (UV) light source that uses UV-C light to destroy the virus. The UV light source and the barrier heater are combined together in a flame retardant and resistant filtration system, which can then be directly integrated into air returns, furnace intakes, and other parts of an air handling system of a facility or populated environ, such as an airport terminal, church, hospital, workshop, office space, residence, transit vehicle, school, hotel, cruise ship, recreational venue, etc. As there is no current cure for COVID-19 and many other pathogens, environmental purification strategies can help slow the spread of the virus, and the air purification provided by the disclosed device can provide a primary defense against transmission.

In one configuration, an apparatus is used with supplied power for treating air flow of an air handing system of a facility. The apparatus comprises a frame, a filter, and an UV light source, and a heater. The frame has a plenum with an inlet and an outlet and is configured to position in the air flow of the air handing system for passage of the air flow therethrough.

The filter is disposed across a surface area of the plenum and comprises a first material, such as a metal. The filter is configured to filter the air flow therethrough up to a filtration threshold. The ultraviolet light source is disposed in the plenum. The ultraviolet light source is connected in electrical communication with the supplied power and is configured to generate an active field of ultraviolet radiation in the plenum. The heater is disposed across the surface area of the plenum and comprises a permeable barrier of metal material. The permeable barrier of the heater is configured to impede the air flow therethrough up to an impedance threshold. Moreover, the permeable barrier of the heater is connected in electrical communication to the supplied power and is heated to a surface temperature.

In another configuration, an apparatus is used with an air filter and supplied power for treating air flow of an air handing system in a facility. The apparatus comprises a frame, a UV light source, and a heater similar to that disclosed above. The filter can be mounted adjacent the frame or separately in the air handling system.

In yet another configuration, a method is used for treating air flow of an air handing system in a facility. A frame is positioned in the air handling system for passage of the air flow therethrough. The air flow is filtered up to a filtration threshold through a filter disposed across a surface area of a plenum of the frame between an inlet and outlet. An active field of ultraviolet radiation is produced in the plenum by powering an ultraviolet light source disposed in the plenum. The air flow is impeded up to an impedance threshold through a permeable barrier of heater disposed across the surface area the plenum and having a metal material. The permeable barrier of the heater is heated to a surface temperature by supplying a voltage potential across the permeable barrier.

The foregoing summary is not intended to summarize each potential embodiment or every aspect of the present disclosure.

DETAILED DESCRIPTION OF THE DISCLOSURE

The subject matter of the present disclosure is directed to a purification device for instantaneously eradicating pathogens, such as COVID-19 virus, from the circulating air by filtering and exposing the pathogens to high temperatures (above 200° C.) (above 392° F.). By doing so, the subject matter of the present disclosure can decrease infectious transmission of a virus and other biological species that may cause future pandemics, while providing a sense of security and peace of mind for the public to return to work, school, life, recreation and healthcare in a post-COVID-19 world.

The primary mechanism of action of the purification device is a specialized heated filter or barrier heater that uses a low energy, targeted thermal conduction of high performance, high resistant porous metal foam incased in a flame retardant frame. The disclosed heated filter or barrier heater can be combined with a highly-efficient HVAC filter. Additionally, ultraviolet light (UV-C) can be added to the system milieu for additive killing effect. Research has shown heat and low wavelength light have been proven to successfully deactivate COVID-19 with duration of exposure.

As disclosed below, the purification device of the present disclosure can be incorporated into air handlings systems of a facility, vehicle, or any other environment. Using the same technology, mobile/robotic COVID-19 purification device can be deployed for use in public venues, healthcare facilities, nursing homes, schools, airplanes, trains, cruise ships, performance venues, theaters, churches, grocery and retail stores, prisons, etc. Details are provided in co-pending U.S. Appl. Ser. No. 16/883,981, entitled "Mobile Purification Device Having Heated Filter for Killing Biological Species, Including COVID-19", which is incorporated herein by reference in its entirety.

Figure 1:
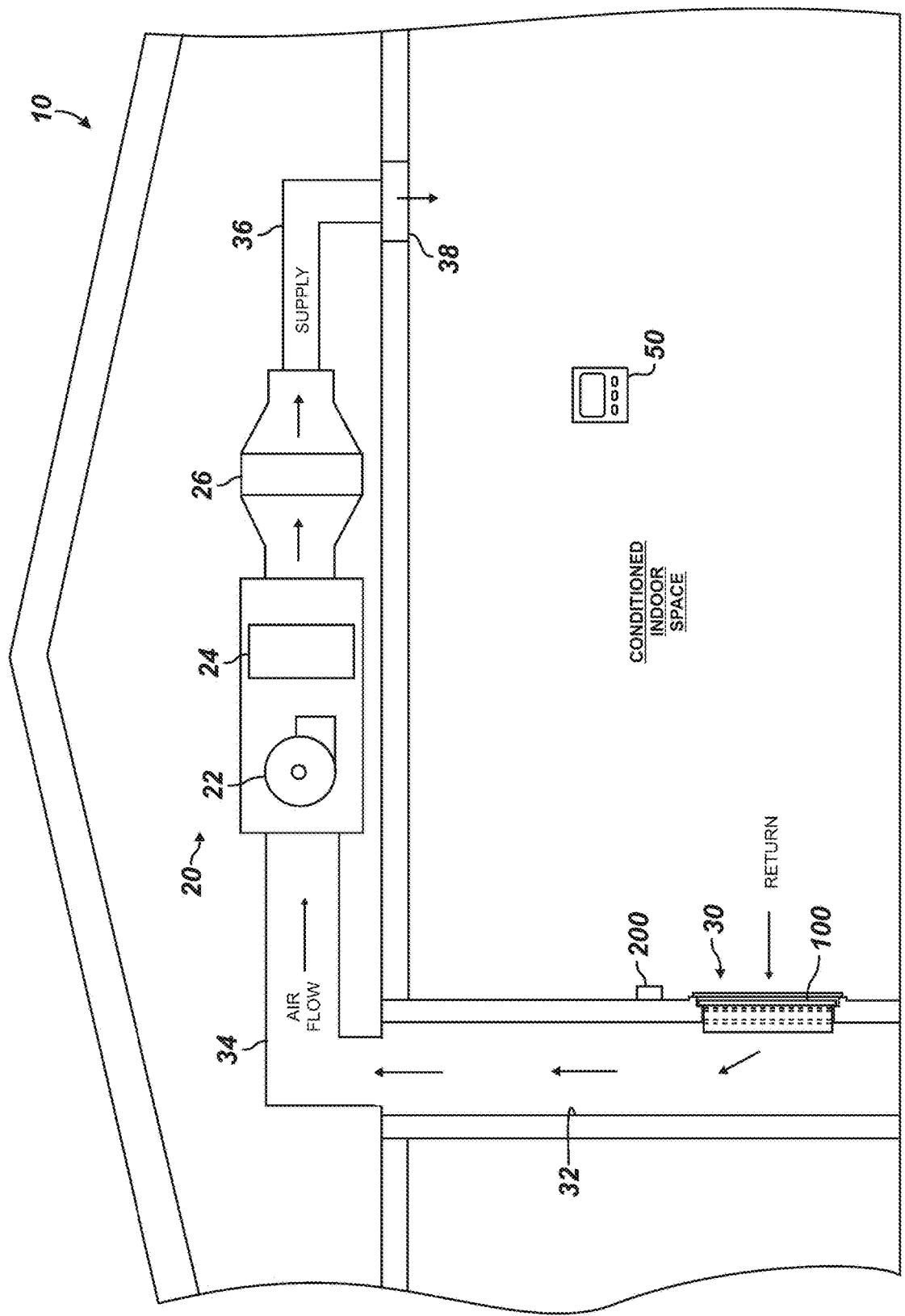
FIG. 1 illustrates a facility having an air handling system having a purification device according to the present disclosure.

As shown in FIG. 1, a facility 10, such as a home, hospital, office space, airport terminal, church, or other enclosed environment, has an air handling system 20. As shown here, the system 20 is a heating, ventilating, and air conditioning (HVAC) system, although other air handling systems can be used. As is typical, the HVAC system 20 includes returns 30, chases 32, return ducts 34, etc. that direct drawn return air from an indoor space to a blower 22, heat exchanger 24, and coiling coil 26 of the system 20. In turn, the system 20 provides conditioned supply air to the space through supply ducts 36, vents 38, and the like. The heat exchanger 24 can include an electric or gas furnace for heating the air. The cooling coil 26 can be an evaporator connected in a cooling circuit to other conventional components outside the facility, such as a condenser, compressor, expansion valve, etc.

Integrated with or incorporated into this system 20, one or more purification devices 100 are used in the facility to purify the air flow. In one arrangement and as shown, the purification device 100 is used in the air return 30 of the HVAC system 20, through which return air is drawn to pass through the conditioning elements of the HVAC system 20. Each air return 30 in a facility may have such a purification device 100 so return air is drawn through the purification device 100 during operation of the HVAC system 20. Because HVAC systems 20 use a number of different filters of various sizes, the purification device 100 can have dimensions to suit various filter sizes.

As discussed in more detail later, the purification device 100 tends to heat the return air with flash heating. For this reason, the device 100 is preferably disposed in the return air upstream of the cooling unit 26. This can allow some of the heat to be dissipated in the air flow before being cooled by the cooling unit 26. When heating the indoor space, the purification device 100 may simply add to the heat provided by the system 20. It is even conceivable that the vents 28 of the system 20 distributing air could have such purification devices 100. However, the devices 100 may tend to diffuse the air flow and pushing air flow through filters is less efficient, making use of the devices 100 in vents possible but less favorable.

Study of airflow in a meeting room and office space shows that convection patterns can persistently carry infection between chairs at a conference table and between cubicles in an open office space. This shows that reliance on separation between people can be ineffective due to the convection of the air.

Control of the purification device 100 can be handled entirely by a local controller 200, which determines independently if air flow is being conducted through the device 100. Alternatively, the local controller 200 can be integrated with a system controller 50 for the HVAC system 20, which can signal activation of the system 20 and indicate to the local controller 200 that air flow is being conducted through the device 100. In a further alternative, the purification device 100 may lack local controls and may be centrally controlled by the system controller 50. As will be appreciated, these control arrangements can be used in any combination throughout a facility 10, multiple purifications devices 100, conditioning zones, HVAC components, and the like.

Although FIG. 1 shows the purification device 100 disposed at the return 30 for the chase 32 of the air handling system 20, other arrangements can be used. Overall, the purification device 100 can be sized for use in a typical furnace opening (14-20 in×25 in) as used commercially. Multiple HVAC zones can then be targeted by the purification device.

Figure 2A:
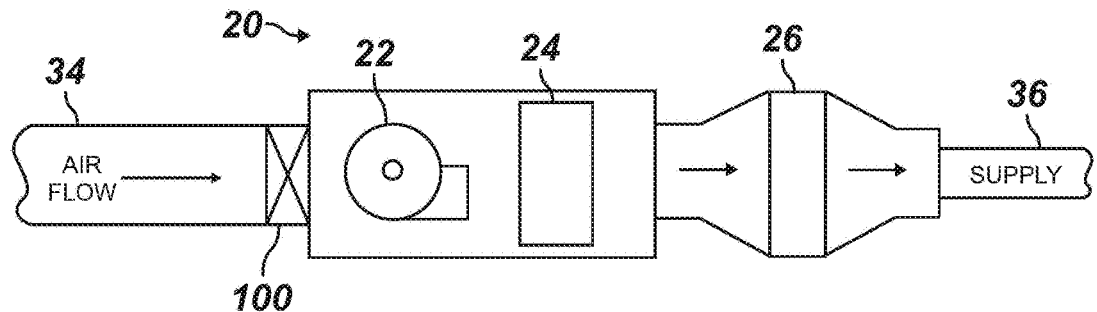
FIGS. 2A, 2B, 2C, 2D, and 2E illustrate other arrangements of the disclosed purification device used with various air handling systems.
Figure 2B:
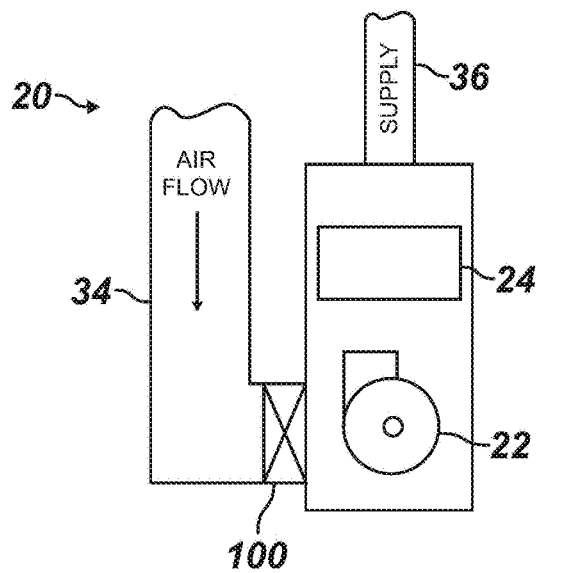
Figure 2C:
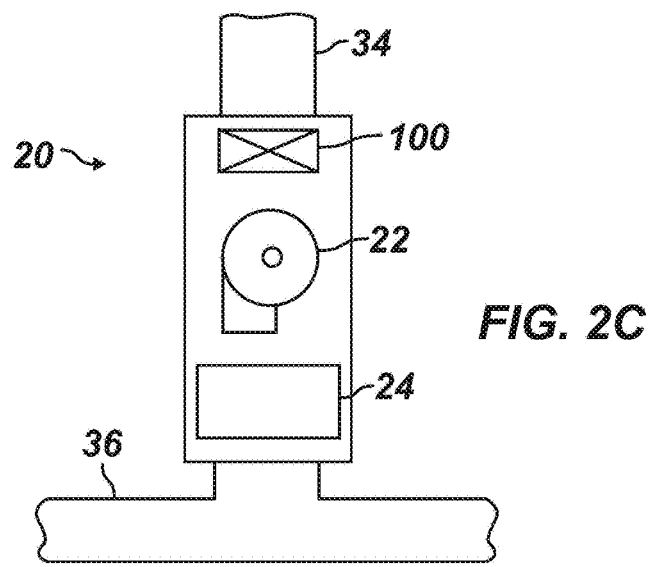

For example, FIG. 2A shows a purification device 100 disposed immediately upstream of the blower 22 and other components of an HVAC system 20, which has a horizontal furnace 24. FIG. 2B shows the purification device 100 disposed adjacent the blower 22 and other components of a system 20, such as a horizontal furnace. Finally, FIG. 2C shows the purification device 100 disposed above the blower in a downflow furnace. These and other configurations can be used. The furnace can use gas burners or electric heating elements as the case may be, and other conditioning components can be installed further downstream.

Figure 2D:
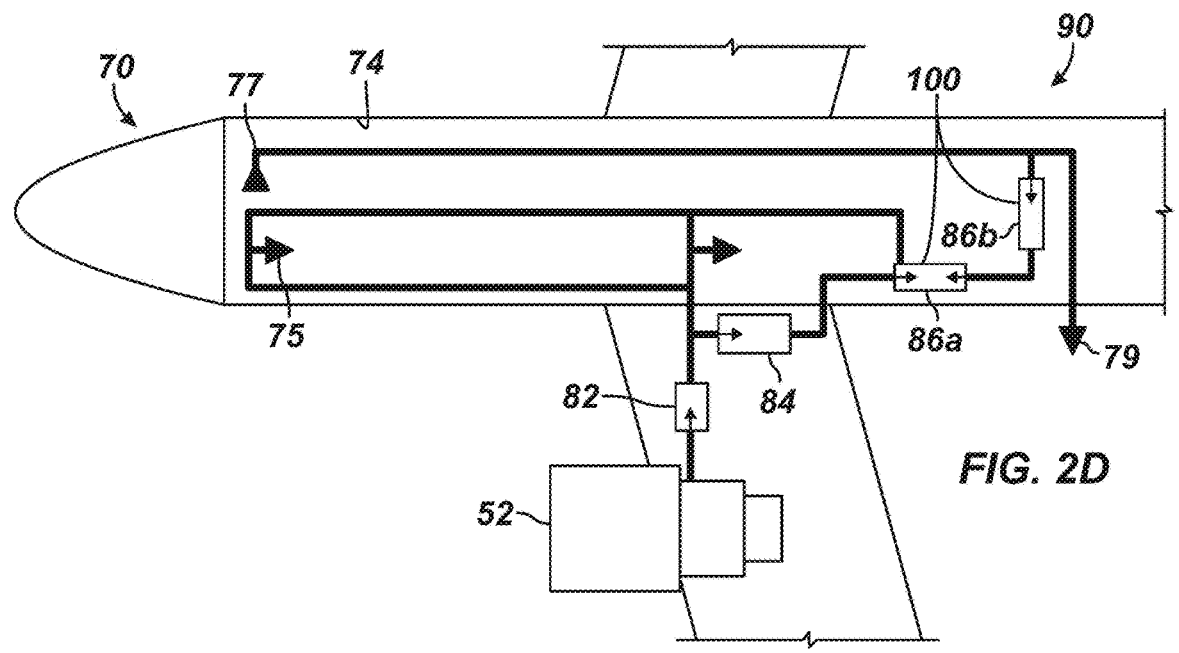

FIG. 2D illustrates an air handling system 80 in an airplane 70 having a purification device 100 of the present disclosure. In the airplane 70, the air in the cabin 74 may be changed 20 to 30 times per hour with about half of the air being recycled through filters. Because the cabin 74 is pressurized, outside air enters an inlet 82 of the system 80 at high temperature and pressure from the engines 72. The hot and compressed air reaches the air conditioning units 84 for the plane 70 where the air is cooled considerably. For heating, some of the input air can enter the cabin 74 though the overhead outlets 75. For cooling, the air from the conditioning unit 84 passes to a mixing manifold 86a, wherein the cooled outside air is combined with cabin air to produce a 50/50 mix. The mixed air from the mixing manifold 86a can then be circulated through the cabin 74 via the overhead outlets 75. A portion of the air in the cabin 74 from inlets 77 is then discharged from outlet 79 in an equal amount to the outside air entering the cabin 74 to maintain a balance, and another portion of the cabin air though a buffer manifold 86b is recirculated in the mixing chamber 86a. Because the outside air is new, the purification device 100 of the present disclosure is placed at the mixing manifold 86a and/or the buffer manifold 86b of the air handling system 80 to treat the recycled cabin air.

Figure 2E:
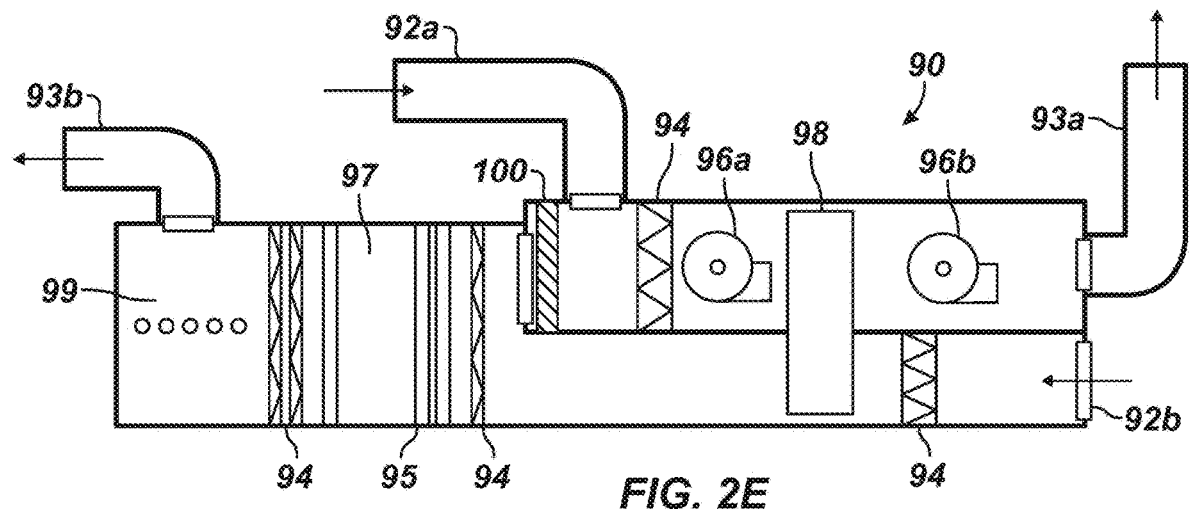

FIG. 2E illustrates an air handling system 90 used in a cruise ship having a purification device 100 of the present disclosure. As shown, return/relief air pulled through a return duct 92a is diverted through filters 94 by blowers 96a, which force the air through a heat wheel 98. Additional blowers 96b then pass air out an exhaust 93a to the atmosphere.

Meanwhile, outside air entering intake 92b passes through filters 94, and the other end of the heat wheel 98 before passing on to cooling and filtering elements. At the return duct 92a, the return/relief air is also diverted to the cooling and filtering elements. For these elements, the air is passed through filters 94, cooling coils 95, UV light treatment 97, additional filters 94, and a steam humidification treatment 99 before passing out to supply air ducts 93b.

As shown in FIG. 2E, the purification device 100 can be used in the return air from the return duct 92a that is recycled back through the system 90. Throughout the cruise ship, various components are used for conducting the air, including duct heaters, axial fans, dampers, etc. Various self-contained unit heaters can also be used in different areas of the cruise ship. Because the cruise ship is much like a facility, the purification device can be incorporated into the various returns, ducts, vents, and standalone units used throughout the vessel.

As will be appreciated, other vehicles and mass transit systems having air handling systems can benefit in a similar way to an airplane and a cruise ship. For example, busses, trains, and subways used in mass transit have air handling systems that typically use both outside air and recycled air. The disclosed purification device 100 can be incorporated into these air handling systems in a comparable way to those discussed above.

Figure 3C:
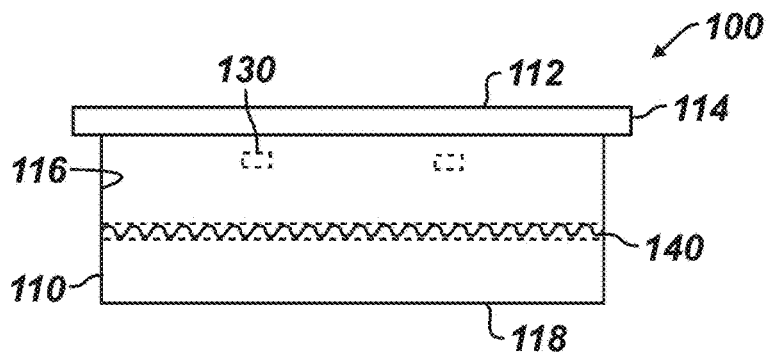
FIGS. 3A, 3B, and 3C illustrate front, side, and end views of a purification device of the present disclosure.
Figure 3A:
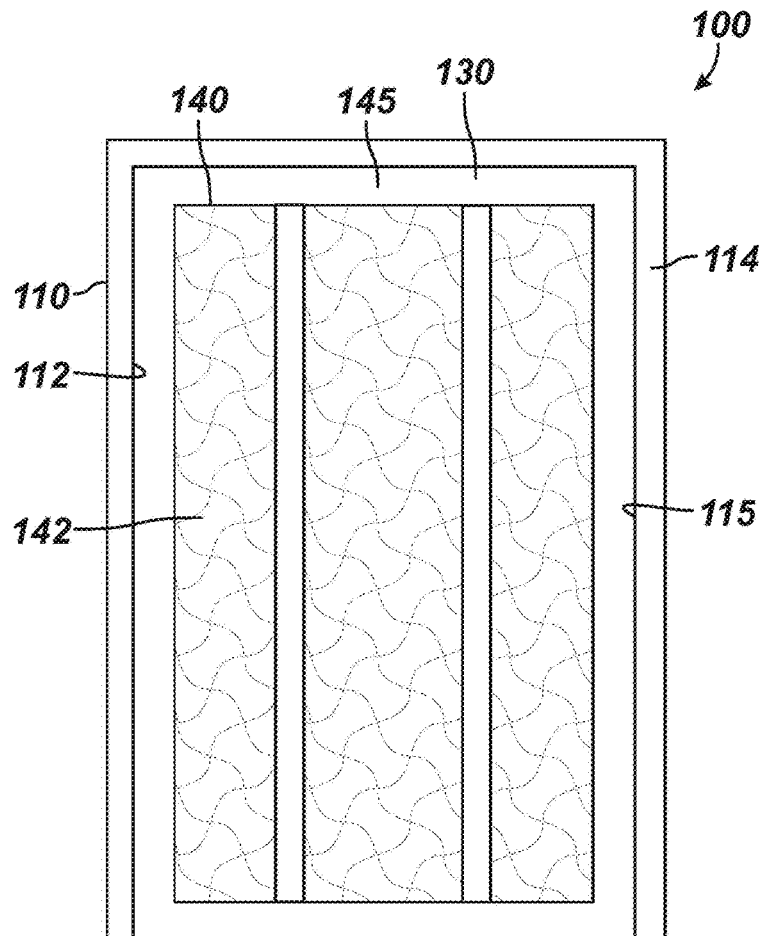
Figure 3B:
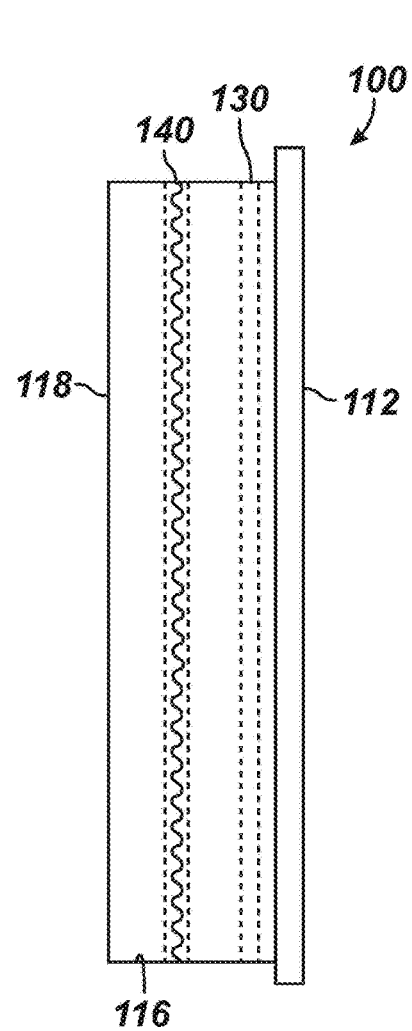

With an understanding of how the purification device 100 is used and where it can be installed in a facility, discussion now turns to particular details of the disclosed purification device 100. FIGS. 3A, 3B, and 3C illustrate front, side, and end views of an example purification device 100 of the present disclosure. The device 100 includes a frame 110 configured for insertion into an existing air return of a facility, for replacing an existing return altogether, or for use at the intake of a furnace.

Overall, the frame 110 has four sidewalls enclosing a plenum inside 116, which is exposed on opposing open faces (one for an inlet 112 and another for an outlet 118 of the plenum 116). If necessary, the inlet 112 can include a rim 114, which would typically engage around a wall opening for a return (30: FIG. 1). Fasteners (not shown) can affix the rim to surrounding structures. Although configured for a particular implementation, a typical size for the frame 110 may include overall dimensions of 20-in width×30-in height×7-in depth.

As best shown in FIG. 3A, the inlet 112 or the rim 114 may form a receptacle for holding a filter (not shown) to filter entering air flow into the plenum 116. Inside the plenum 116, the frame 110 holds a barrier heater 140. As briefly shown here, the barrier heater 140 includes a permeable barrier 142, composed of metal and comprising a mesh, a foam, a screen, or a tortuous media, supported by a surrounding case 145 and disposed across the plenum 116 to provide a permeable surface area for treating the air flow as discussed below.

Also inside the plenum 116, the frame can hold an UV light source 130 as an additional treatment in conjunction with the barrier heater 140. (Other embodiments disclosed herein may not include the UV light source 130.) As briefly shown here, the UV light source 130 includes two UV-C light emitting diode (LED) strips placed across the plenum 116 to provide an active field for treating the air flow as discussed below. More or fewer sources 130 can be used, and different types of sources 130 can be installed.

Figure 4A:
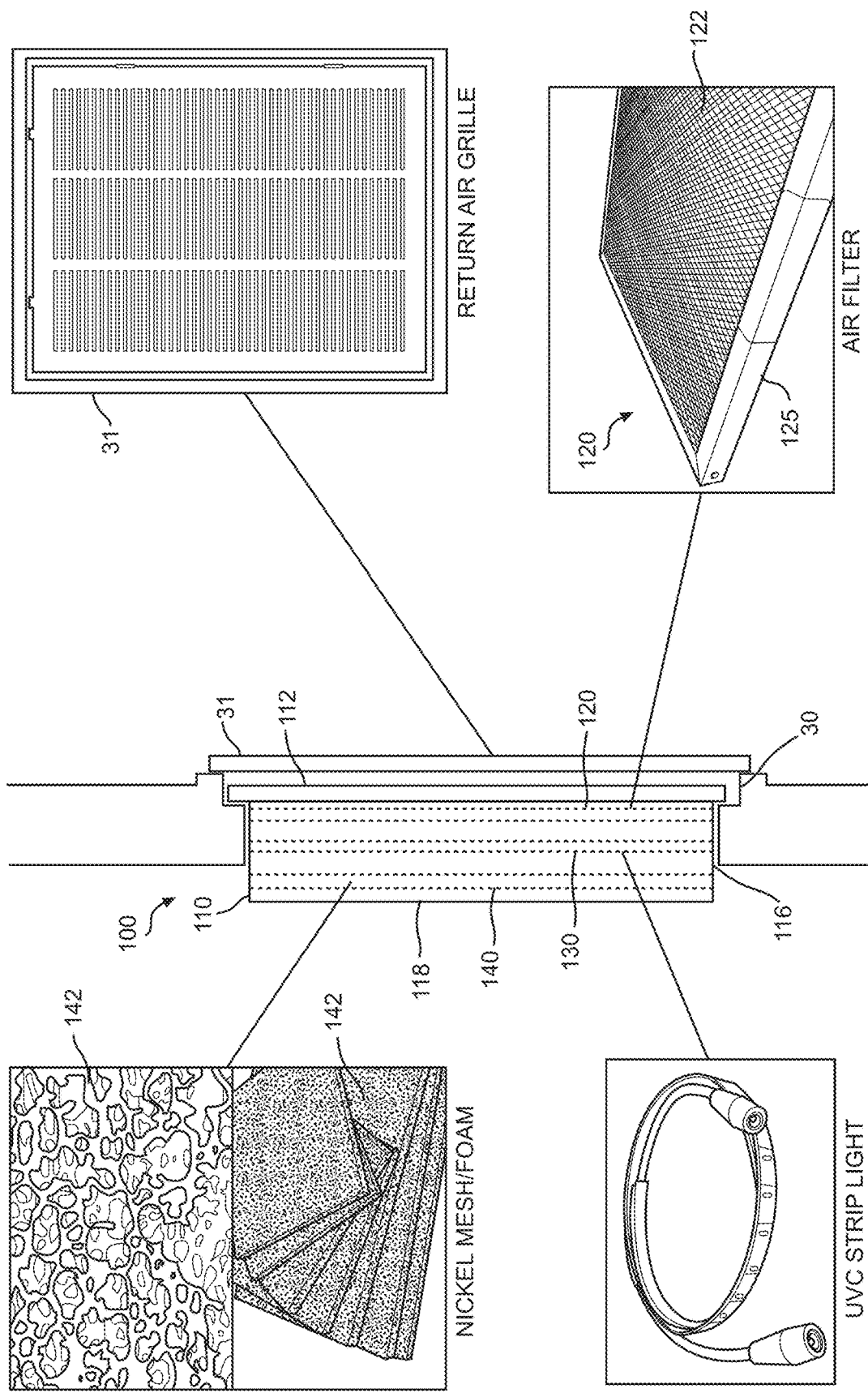
FIGS. 4A and 4B illustrate side schematic views of a purification device with an arrangement of its components.

Turning to FIG. 4A, a side schematic view of a purification device 100 is shown having an arrangement of its components. As noted previously, the purification device 100 can be used in a return 30 of an air handling system. The wall opening of the return 30 may typical have a return air grille 31 to protect internal components. The frame 110 of the purification device 100 fits in the return 30 and can be held by fixtures (not shown), such as bolts and screws. As noted, the air filter 120 can fit into a receptacle of the frame 110. Typically, the filter 120 simply fits snuggly in the receptacle, but fastening could be used.

Preferably, the purification device 100 first filters the air flow up to a filtration threshold through the filter 120. In this way, the filter 120 can keep out dust and other particulates from being drawn into purification device 100 and from being drawing further into the HVAC system (20: FIG. 1).

As noted herein, an active field of ultraviolet radiation can be produced in the plenum 116 of the device 100 by powering the UV light source 130 disposed in the plenum 116. In the plenum of the device 100, the air flow is impeded up to an impedance threshold through the barrier heater 140 disposed in the plenum 116. The barrier heater 140 includes a permeable barrier 142 (e.g., mesh, foam, screen, tortuous media) of a metal material, such as nickel, nickel alloy, titanium, steel alloy, or other metal material. The permeable barrier 142 can be flat, corrugated, bent, pleated, or the like and can be arranged in one or more layers. The metal mesh/foam 142 of the heater 140 is heated to a surface temperature by supplying a voltage potential across the mesh/foam. Preferably, the UV light source 130 is disposed in the plenum 116 between the filter 120 and the barrier heater 140 so that the irradiation from the source 130 can treat passing air flow and can also treat exposed surfaces of the filter 120 and the barrier heater 140.

Figure 4B:
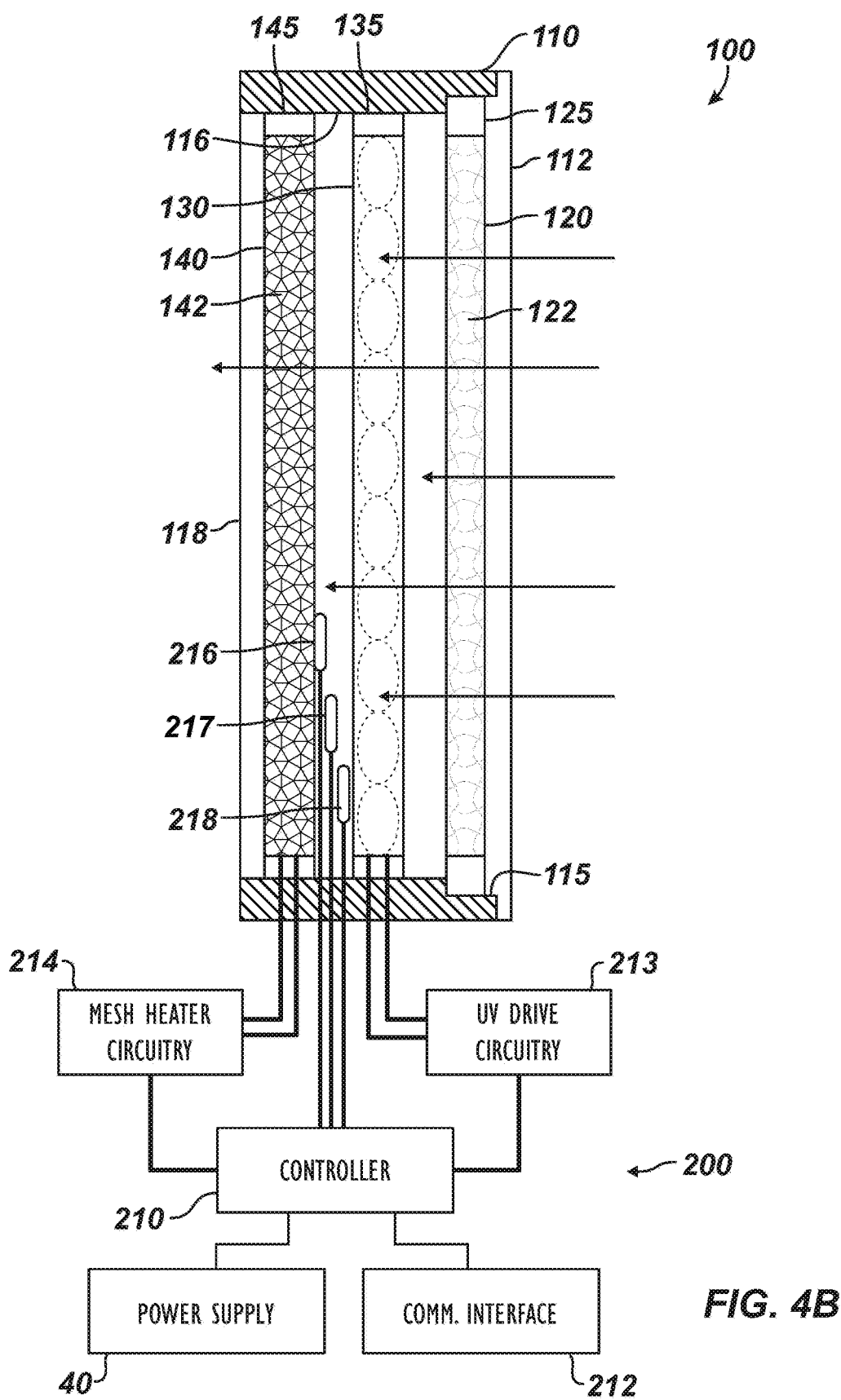

Turning now to FIG. 4B, another side schematic view of a purification device 100 is shown having an arrangement of its components. The frame 110 of the device 100 is shown holding the filter 120, UV light source 130, and barrier heater 140 in the plenum 116. The purification device 100 is used with control circuitry and supplied power. For example, the control circuitry includes a controller 200 having appropriate power circuitry and processing circuitry for powering and controlling the purification device 100. The controller 200 can be connected to one or more types of power supply(s) 40, such as available AC power supplies of a facility, battery power, or other power source. Power circuitry of the controller 200 can convert the supplied power as needed to produce DC power and voltage levels.

Looking at the frame 110, the filter 120 is disposed in the plenum 116 of the frame 110 and can be held in a receptacle 115 toward the inlet 112. The filter 120 is composed of a first material and is configured to filter the air flow therethrough up to a filtration threshold. Preferably, the filter 120 is a metal filter media 122 composed of stainless steel, aluminum, etc. that is meshed in one or more layers depending on the amount of air flow and the level of filtration required. The filter 120 has a case 125, which is also composed of metal and which frames the metal filter media. In general, the metal filter 120 can be a 1-in thick HVAC filter made from metal that is fire resistant and retardant and that has a high efficiency rating.

The barrier heater 140 is also disposed in the plenum 116 and can be situated toward the outlet 118. Insulation 145 for both heat and electricity may separate the barrier heater 140 from the frame 110. The barrier heater 140 includes a mesh/foam of a metal material and is configured to impede the air flow therethrough up to an impedance threshold.

The UV light source 130 can be disposed in the plenum 116 and, as noted previously, can preferably be situated between the metal filter 120 and barrier heater 140. The UV light source 130 produces an active field of UV-C light in the plenum 116 to treat passing air flow. As noted herein, pathogens, such as viruses, can be eliminated when subjected to a dose of ultraviolet light. For example, the sRNA coronavirus up to 0.11 µm in size can be eliminated >99% with only about 611 µj/cm$^2$ UVGI dose.

Both the UV light source 130 and the barrier heater 140 are connected in electrical communication with the power supply 40 through the controller 200, which controls the illumination of the light source 130 and the heating of the barrier heater 140 in the plenum 116.

The UV light source 130 can include one or more UV-C lamps, a plurality of light emitting diodes, or the like disposed in the plenum 116. For example, the source 130 can use one or more Ultraviolet Germicidal lamps, such as mercury-vapor lamps. The source 130 can also use light emitting diodes having semiconductors to emit UV-C radiation.

One or more structures can be disposed in the frame 110 to support the UV light source 140. The structures used can depend on the type of source 140 used and can include fixtures for lamps and strips for UV-C LEDs. For example, the UV light source 130 can uses several strips of UV-C light emitting diodes stretched across the plenum 116.

The effectiveness of the UVGI treatment in the air flow depends on a number of factors, including the targeted microbial species, the intensity of the exposure, the time of the exposure, and the amount of humidity in the air. A sufficient dose will kill the DNA-based microorganism. Therefore, the intensity of the UVGI treatment, the time for exposure, and other factors can be configured and further controlled in the purification device 100 and HVAC system to reach a desired effectiveness.

The UVGI treatment provided by the purification device 100 can be effective at destroying pathogens, such as COVID-19. The UV-C or short-wave light generated by the UV light source at wavelengths from 100-280 nanometers may have a proven germicidal effect. In particular, 222 nanometer low, far-UVC light is effective at killing and deactivating aerosolized virus with duration of exposure.

In contrast to conventional use of UVGI in an HVAC system, the disclosed purification device 100 does not require high costs and special installation in air returns or duct systems. Rather, the disclosed device 100 offers practical installation and operation that can be seen as easy as changing an HVAC filter every 1-3 months in your home.

As discussed in more detail below, the metal permeable barrier of the barrier heater 140 can include nickel mesh/foam. The barrier heater 140 is configured to impede the air flow therethrough up to the impedance threshold of 20 percent, giving the foam a porosity of at least 80%.

The purification device 100 can include anti-microbial coatings on one or more surfaces to eliminate live bacteria and viruses. For example, the filter 120 can have an anti-microbial coating to eliminate pathogens trapped by the filter media. The inside walls of the frame's plenum 116 can also have anti-microbial coating. If practical under heated conditions, the mesh/foam of the barrier heater 140 can have anti-microbial coating.

As further shown in FIG. 4B, the controller 200 disposed in electrical communication with the UV light source 130 and the barrier heater 140 is configured to control (i) the radiation of the UV light source 130 powered by the power supply 40, and (ii) the heating of the barrier heater 140 by the power supply 40. This controller 200 can be a local controller that can include a communication interface 212 to communicate with other purification devices and with other components of an air handing system (20: FIG. 1) in a facility, such as a system controller (50). The local controller 200 can receive a signal that the HVAC system (20) is on/off, which is indicative of the passage of the air flow through the device 100. The controller 200 can then the control the heating of the barrier heater 140 and the illumination of the UV light source 130 based on the signals received.

To do this, the controller 200 is disposed in electrical communication with heater circuitry 214 connected to the barrier heater 140. At least for a period of time when air is passed through the device 100 (being drawn by the HVAC system), the controller 200 can control the heating of the barrier heater 140 with the heater circuitry 214 powered by the power supply 40. As will be appreciated, the controller 200 and heater circuitry 214 includes any necessary switches, relays, timers, power transformers, etc. to condition and control power supplied to the barrier heater 140.

The controller 200 heats the barrier heater 140 at least while the controller 200 is signaled that the HVAC system (20) is operating indicating air flow through the device 100. Pre-heating before the HVAC system (20) draws return air can occur before air is drawn through the device 100 so that a target temperature can be reached beforehand. This may require an advance signal from the system controller (50) or may involve intermittent heating of the barrier heater 140 to maintain some base temperature. Post-heating after the HVAC system (20) turns off may also be beneficial for a number of reasons.

The controller 200 is also disposed in electrical communication with drive circuitry 213 connected to the UV light source 130. At least for a period of time when air is passed through the device 100 (being drawn by the HVAC system), the controller 200 can control the illumination of the UV light source 130 with the drive circuitry 213 powered by the power supply 40. As will be appreciated, the controller 200 and drive circuitry 213 includes any necessary switches, relays, timers, power transformers, electronic ballast, etc. to condition and control power supplied to the light source 130.

At least when the controller 200 is signaled that the HVAC system (20) is operating indicating air flow through the device 100, the controller 200 illuminates the light source 130. To reach a target illumination, some pre-lighting may be necessary for the lamps or the like of the UV light source 130 to reach full illumination before air is drawn through the device 100. This may require an advance signal from the system controller (50). Post-lighting of the source 130 after the HVAC system (20) turns off may also be beneficial for a number of reasons.

For monitoring and control, the controller 200 can include one or more sensors 216, 217, and 218. For example, the controller 200 can include a temperature sensor 216 disposed in the plenum 116 adjacent the barrier heater 140 and disposed in electrical communication with the controller 200. The temperature sensor 216 is configured to measure temperature associated with the heating of the barrier heater 140 so the controller 200 can reach a target temperature. Depending on the implementation and the pathogens to be affected, the barrier heater 140 can heated to the surface temperature over about 54° C. (130° F.). In fact, research shows that heat at about 56° C. or above 56-67° C. (133-152° F.) can kill the SARS coronavirus and that 222-nanometer far-UVC light can be effective at killing and deactivating aerosolized virus.

The controller 200 can be connected to a light sensor 28, such as a photocell or other light sensing element, to monitor the illumination, intensity, wavelength, operation, and the like of the UV light source 130. For example, the UV light source 130 can be configured to produce the ultraviolet radiation with at least 611 µJ/cm2 dose of ultraviolet germicidal irradiation in an active field in the plenum 116, and measurements from the light sensor 218 can monitor the radiation.

The controller 200 can be connected to yet another sensor 217, such as a flow sensor to sense flow, velocity, and the like of the air passing through the plenum 116. The detected flow by the flow sensor 217 may be used by the controller 200 to initiate operation of the device 100 if not signaled remotely. The velocity of the flow may be measured by the flow sensor 217 to coordinate a target flow velocity through the device 100 so the heating of the air flow by the barrier heater 140 can be coordinated to the detected flow velocity and a target heating level. Should the device 100 be integrated with the HVAC system (20) operable at different flow levels, then feedback from the flow sensor 217 can be used to control or indicated the level of drawn air through the device 100. The velocity of the flow may also be monitored to coordinate the target irradiation of the air flow by the UV light source 140 so appropriate exposure levels can be achieved.

Figure 4C:
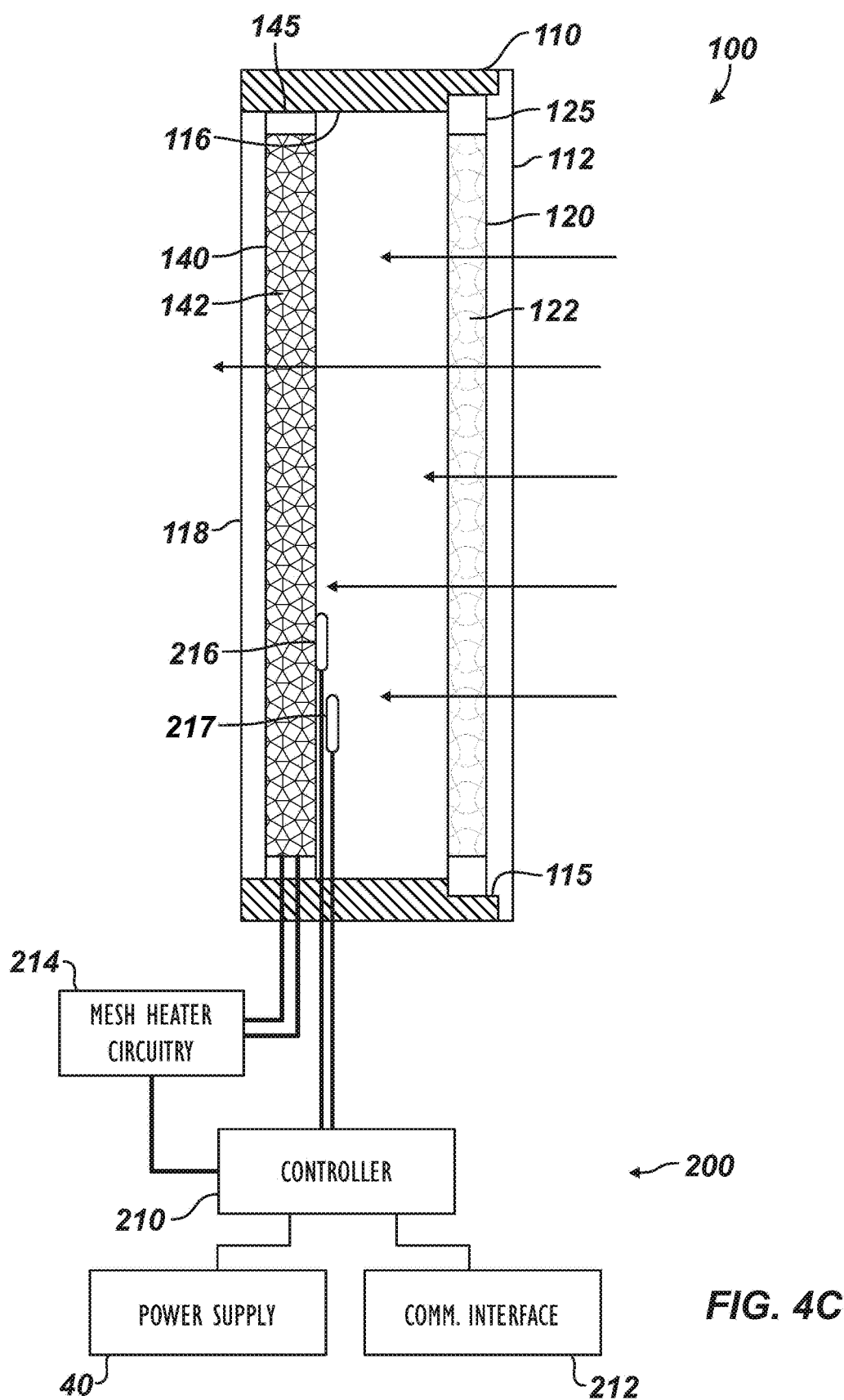
FIG. 4C illustrates a side schematic view of another purification device with an arrangement of its components.

As noted herein, the purification device 100 combines thermal energy with UV-C light and is constructed within a flame retardant and resistant filtration system. The device 100 can be placed in a return behind the HVAC grill for return air. As disclosed herein, embodiments of the purification device 100 include the barrier heater 140 and can thereby include the various features of the controller 200, sensors, etc. discussed above for the barrier heater 140. Some embodiments may not include the UV light source 130, while other embodiments may include the UV light source 130 along with the various features of the controller 200, sensors, etc. discussed above for the UV light source 130. In particular, FIG. 4C illustrates another side schematic view of a purification device 100 having an arrangement of its components without a UV light source. Similar components are provided the same reference numerals as other embodiments and are not repeated here.

As proposed, the disclosed purification device 100 can eliminate pathogens, such as COVID-19, while filtering the air to 99.97% (ASME, U.S. DOE) of particles. As disclosed in the co-pending application incorporated herein, the configuration can be combined into a mobile housing for use at larger public venues to include airport terminals, churches, hospitals and other enclosed areas to reduce infectious air particles.

Although the purification device 100 has been described above as including a frame 110 that accommodates an air filter in the frame 110. The device 100 can include a frame 110 that mounts behind a conventional air return 30 already accommodating a filter. Alternatively, the device 100 can include a frame 110 that mounts at an intake of a furnace downstream from a separately held air filter 120. The purification device 100 can be sized to a furnace opening (e.g., 14-20 in×25 in) for commercial use. HVAC zones can then be targeted. In this types of arrangement, the purification device 100 can include a frame 110, an UV light source 130, and a barrier heater 140 as before, but the frame 110 does not necessarily hold or receive an air filter 120. Instead, separate air filters can be installed elsewhere in the HVAC system, such as at returns.

Discussion now turns to details of the barrier heater 140 of the disclosed purification device 100. The metal mesh/foam of the barrier heater 140 can have one or more layers of material and can have a suitable thickness. As one example, the mesh/foam may have thickness of 0.5 mm to 2.0 mm. Composed of nickel (Ni), the metal mesh/foam may have surface charge density (a) of $1.43 \times 10^7$ C/m². The Ni mesh/foam is electrically conductive, and it is highly-porous having random three-dimensional channels defined therethrough. The mesh/foam exhibits resistance of about 00.1780, and the electrical resistivity of an exemplary Ni foam is calculated to be about $1.51 \times 10^{-5}$ Ωm.

Figure 5A:
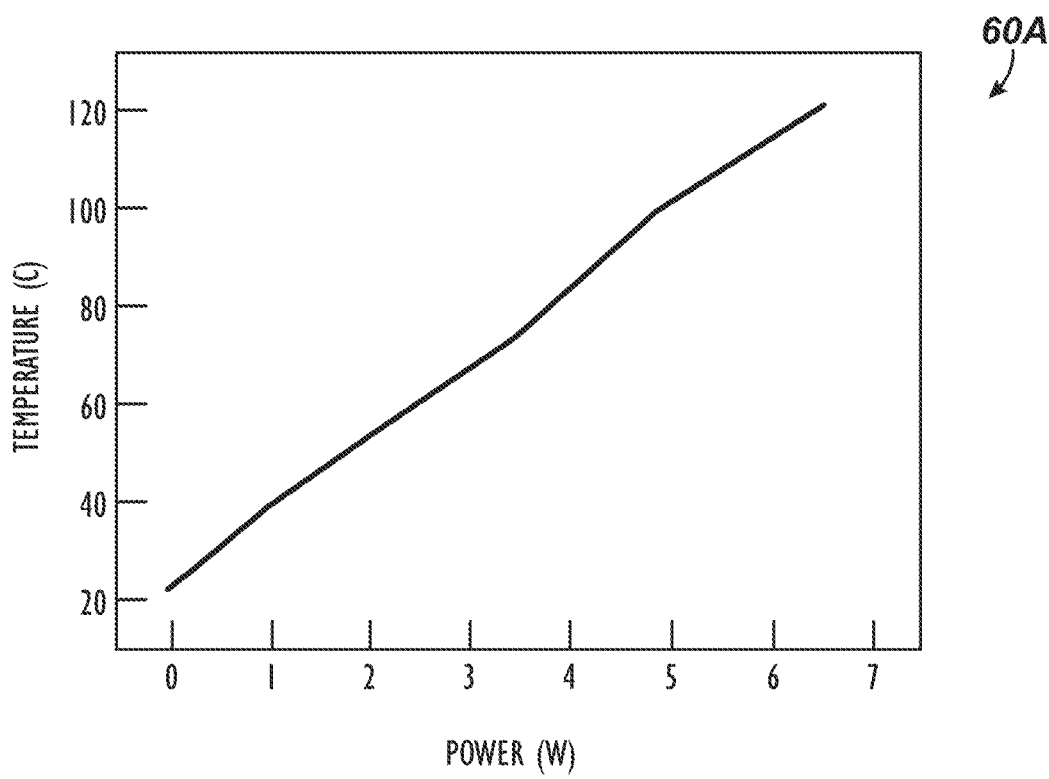
FIGS. 5A, 5B, and 5C illustrate graphs detailing features of a barrier heater for the disclosed purification device.

For example, FIG. 5A illustrates a first graph 60A of the temperature (° C.) produced by an exemplary Ni foam material for the barrier heater per unit of supplied power (W). A sample of the foam having a size of 1.65 mm×195 mm×10 mm was investigated. The temperature was measured after applying voltage until the temperature became stable. As shown in the graph 60A, the temperature is shown to rise generally linearly per unit supplied power so that about 7 watts produces a temperature of about 120° C. (248° F.).

Figure 5B:
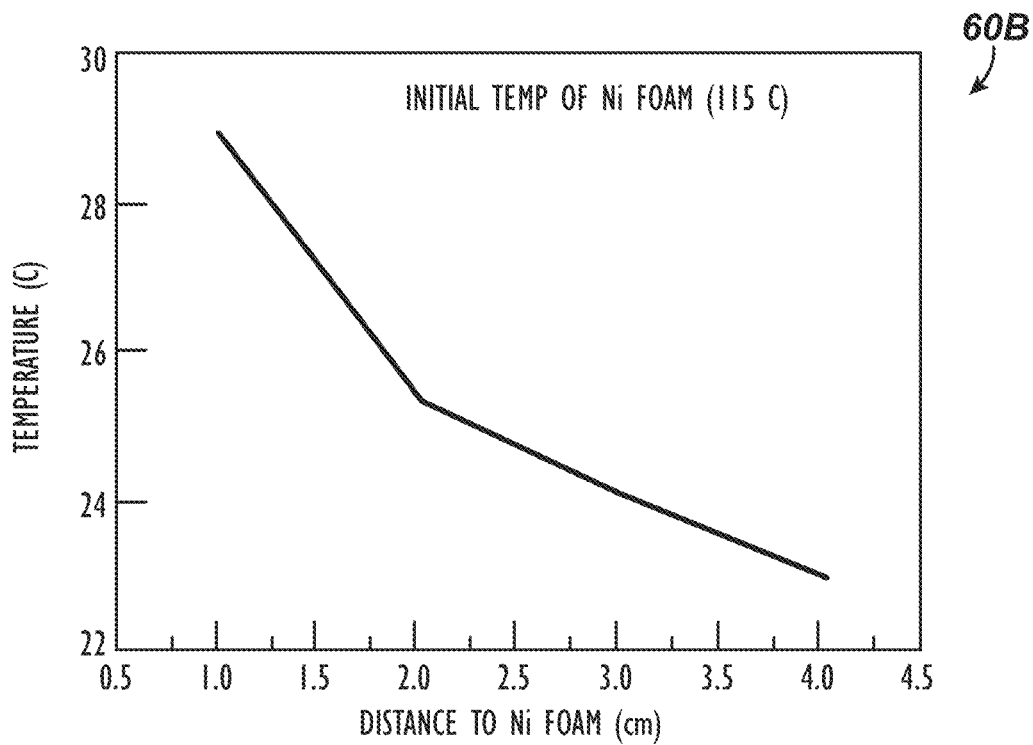

FIG. 5B illustrates a second graph 60B of the measured temperature of gas (e.g., $N_2$) after flowing through the exemplary Ni foam material for the barrier heater heated to a temperature. The gas for the measurement was originated from an upstream distance of about 3.5 cm from the heated Ni foam material while room temperatures was about 21.7° C. (71° F.). Temperature measurements were made at different downstream distances relative to the exemplary Ni foam material, which was heated to an initial temperature of about 115° C. (239° F.). As can be seen, the measured temperature of the gas decreased from about 29° C. to 23° C. (84° F. to 73° F.) for downstream distances ranging from 1 cm to 4 cm from the exemplary Ni foam material. This indicates that the heating produced by the barrier heater 140 composed of such an exemplary Ni foam material provides a tortuous heated surface area against which the air flow and any pathogens can impact, but the heating is localized and dissipated in the downstream air flow.

Figure 5C:
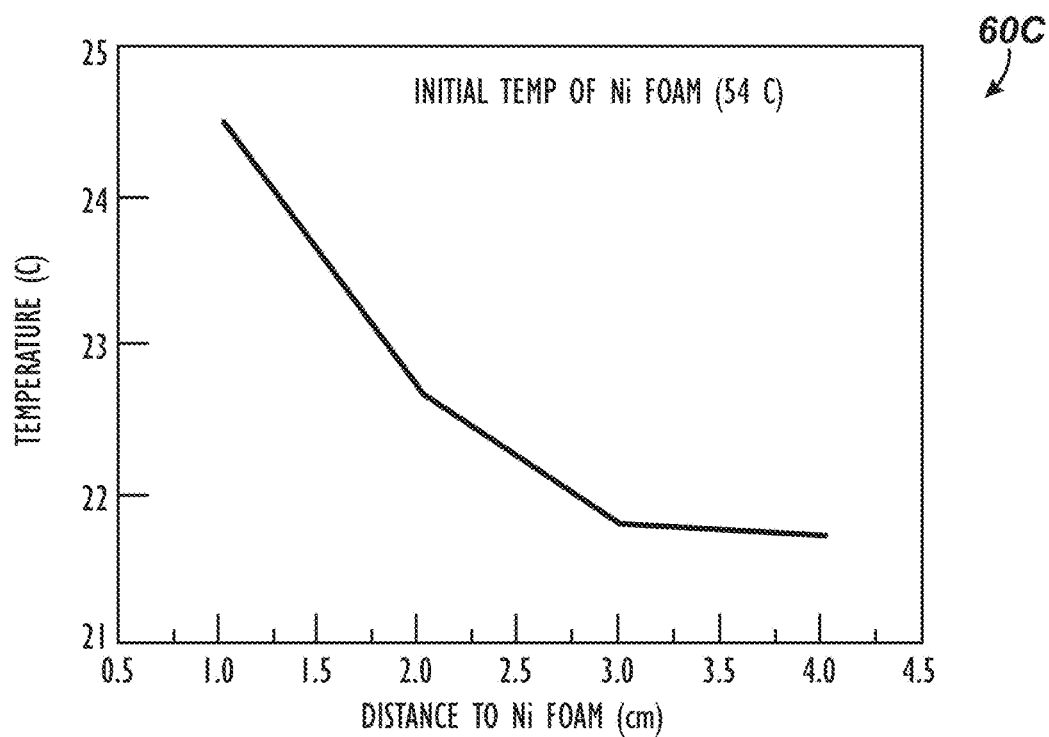

FIG. 5C illustrates another graph 60C of the measured temperature made at different downstream distances relative to the exemplary Ni foam material at another initial temperature. Here, the Ni foam material is at an initial temperatures of about 54° C. (129° F.). The measured temperature of the gas decreased from about 24.5° C. to 21.7° C. (76° F. to 71° F.) for distances ranging from 1 cm to 4 cm from the exemplary Ni foam material.

As noted herein, the barrier heater 140 can use nickel, but could use nickel-based alloys or iron-based alloys developed for applications at high service temperatures and in corrosive environments. Nickel is slowly oxidized by air at room temperature and is considered corrosion-resistant. Nickel is a high performance metal that can be easily regulated to reach high temperatures with minimal transmission of heat to its surroundings or to air molecules passing through it. When voltage is passed through nickel mesh/foam ($1.43 \times 10^7$ σ), for example, the metal conducts energy to a target temperature hot enough to kill pathogens, including COVID-19 on contact. The target temperature can be (56° C. to 66° C. or more, and even over 93° C.) (133° F. to 150° F. or more, and even over 200° F.). In this way, the Ni mesh/foam (0.5 mm-2.0 mm) provides a heated, charged surface area for the pathogen to impact and be eliminated by the heated latticework. Meanwhile, the porosity (80-90%) of the foam/mesh of the barrier heater 140 does not overly impede the air flow and does not detrimentally increase the energy required from the HVAC system.

As disclosed above, heating in the plenum 116 can be achieved with the barrier heater 140 having the mesh/foam that is heated to the target temperature and provides a tortuous path for return air passing through the mesh/foam. Other forms of heating can be used. As disclosed above, UV illumination in the plenum 116 can be achieved with UV light strips. Other forms of UV illumination can be used.

Figure 6A:
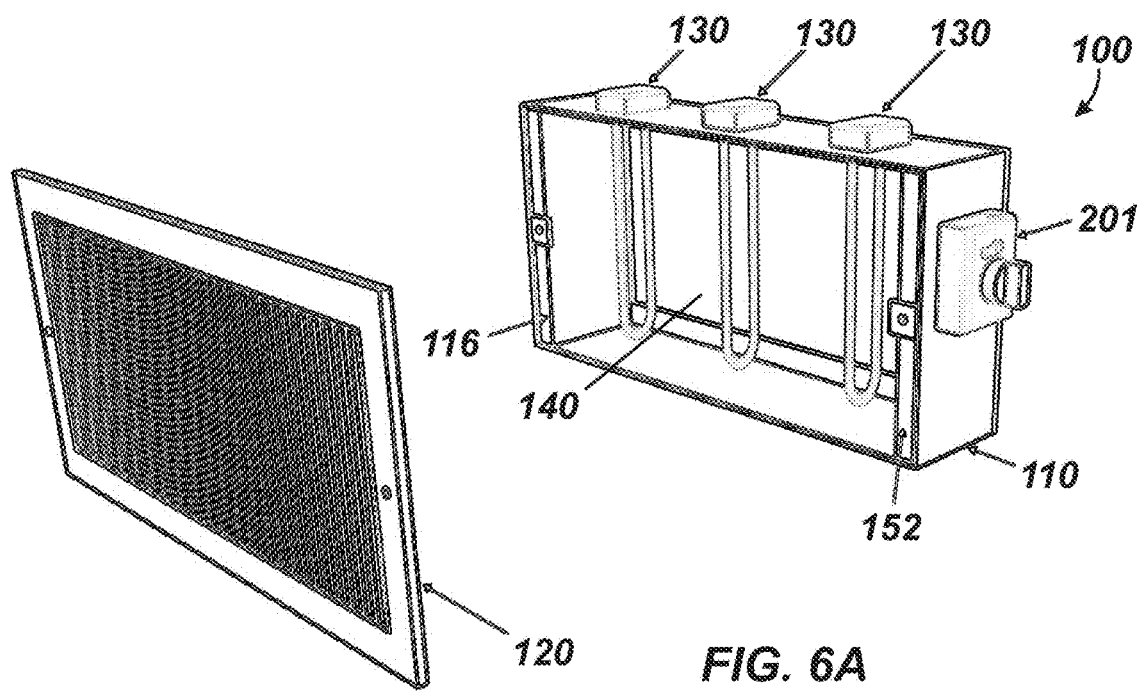
FIG. 6A illustrates another heating arrangement having a plurality of electric elements disposed in a plenum of a frame and connected to a power source control.

For example, FIG. 6A shows another arrangement having a plurality of electric elements (UV light sources 130 and a barrier heater 140) disposed in a plenum 116 of a frame 110 and connected to a power source control 201. The plenum 116 includes carbon media 152 on one or more sidewalls for absorption and purification purposes. The plenum 116 may also include a filter 120 that is disposed at the inlet.

Figure 6B:
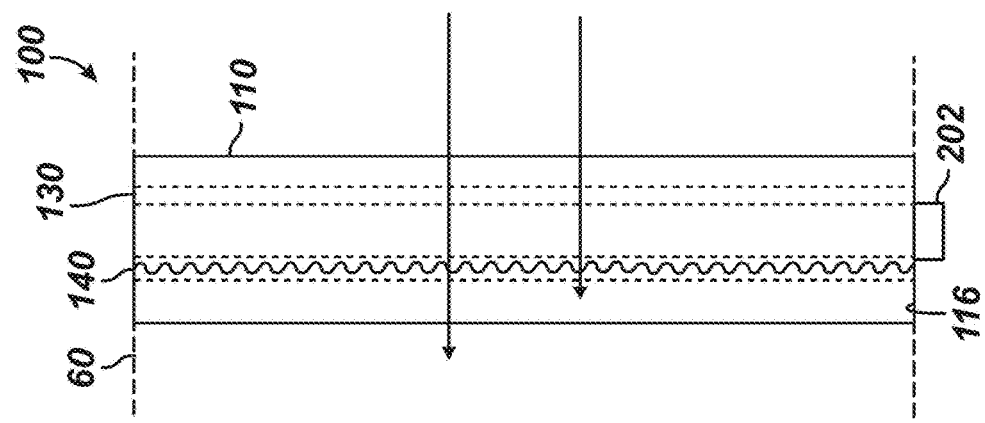
FIGS. 6B, 6C, and 6D illustrate other configurations of the disclosed purification device.

As hinted to above, the disclosed purification device 100 can be used separately or in combination with an air handling system and other purification devices 100. As one example, FIG. 6B shows a configuration of a purification device 100 according to the present disclosure, which includes a UV light source 130 and a barrier heater 140 controlled by control/power circuitry 202. The UV light source 130 and the barrier heater 140 can be similar to those disclosed herein and can be housed together in a housing or frame 110 to fit into the air flow of an air handling system. For example, the housing or frame 110 can be retrofitted or added to an existing duct of the air handling system, can be disposed upstream of operable components of the air handling system, or can be configured elsewhere in the air flow. Filtering can be achieved elsewhere in the air handling system. For its part, the control/power circuitry 201 may have the necessary components as disclosed herein to control the UV light source 130 and the barrier heater 140.

Figure 6C:
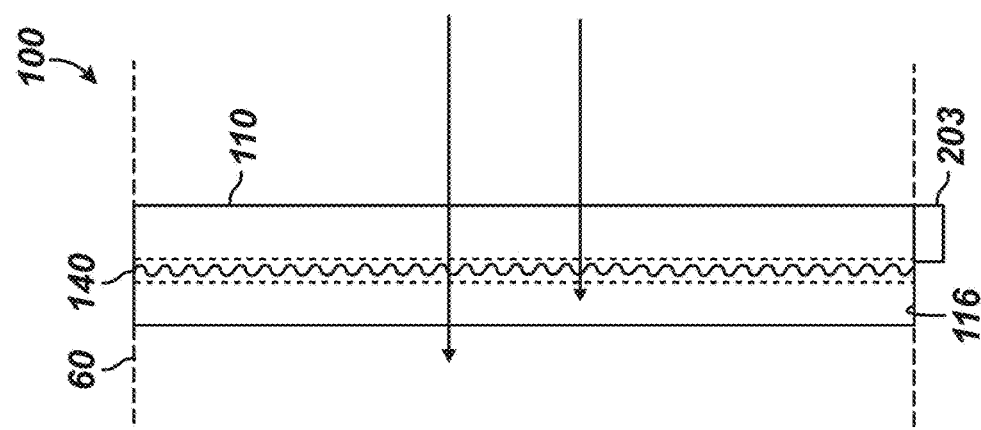

As another example, FIG. 6C shows another configuration of a purification device 100 according to the present disclosure, which includes a barrier heater 140 controlled by control/power circuitry 203. This device 100 as shown may not include a UV light source, although such a source could be used elsewhere in a facility or other environment. The barrier heater 140 can be similar to those disclosed herein and can be housed in a housing or frame 110 to fit into the air flow of an air handling system. For example, the housing or frame 110 can be retrofitted or added to an existing duct of the air handling system, can be disposed upstream of operable components of the air handling system, or can be configured elsewhere in the air flow. Filtering can be achieved elsewhere in the air handling system or can be incorporated into the frame 110 using a filter (not shown) as disclosed elsewhere herein. For its part, the control/power circuitry 203 may have the necessary components as disclosed herein to control the barrier heater 140.

Figure 6D:
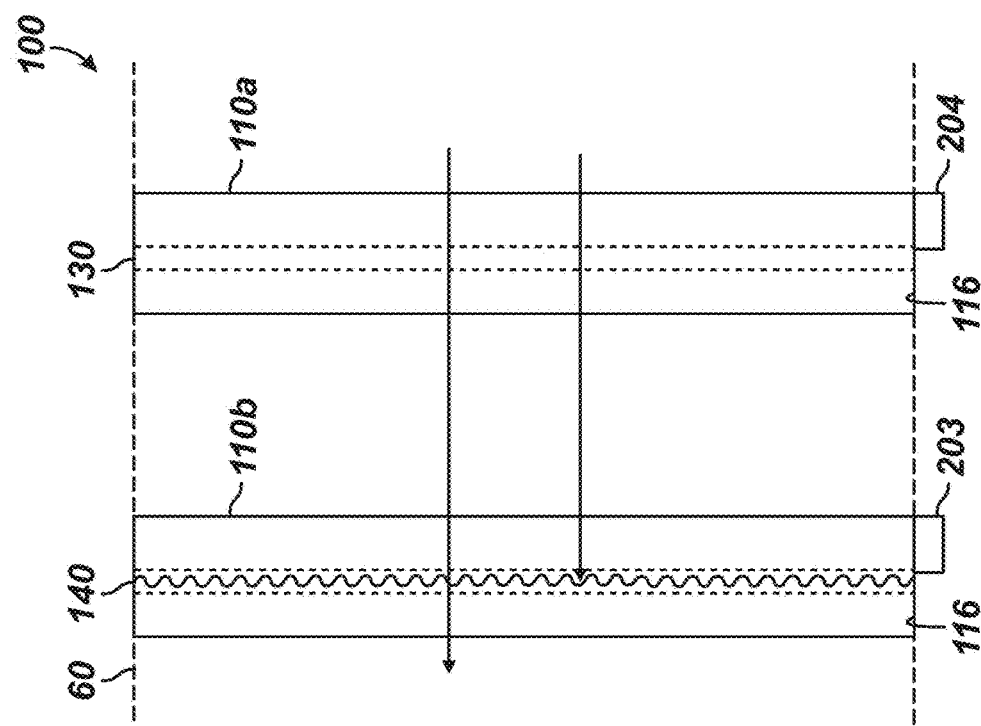

As yet another example, FIG. 6D shows yet another configuration of a purification device 100 according to the present disclosure, which includes a UV light source 130 controlled by control/power circuitry 204 and includes a barrier heater 140 controlled by control/power circuitry 203. The UV light source 130 and the barrier heater 140 can be similar to those disclosed herein and can be housed in separate housings or frames 110a-b to fit into the air flow of an air handling system. For example, the housings or frames 110a-b can be retrofitted or added to existing ducts of the air handling system, can be disposed upstream of operable components of the air handling system, or can be configured elsewhere in the air flow. Filtering can be achieved elsewhere in the air handling system or can be incorporated into either one or both of the frames 110a-b using a filter (not shown) as disclosed elsewhere herein. For their parts, the control/power circuitry 203, 204 may have the necessary components as disclosed herein to control the UV light source 130 and the barrier heater 140 respectively.

Figure 7:
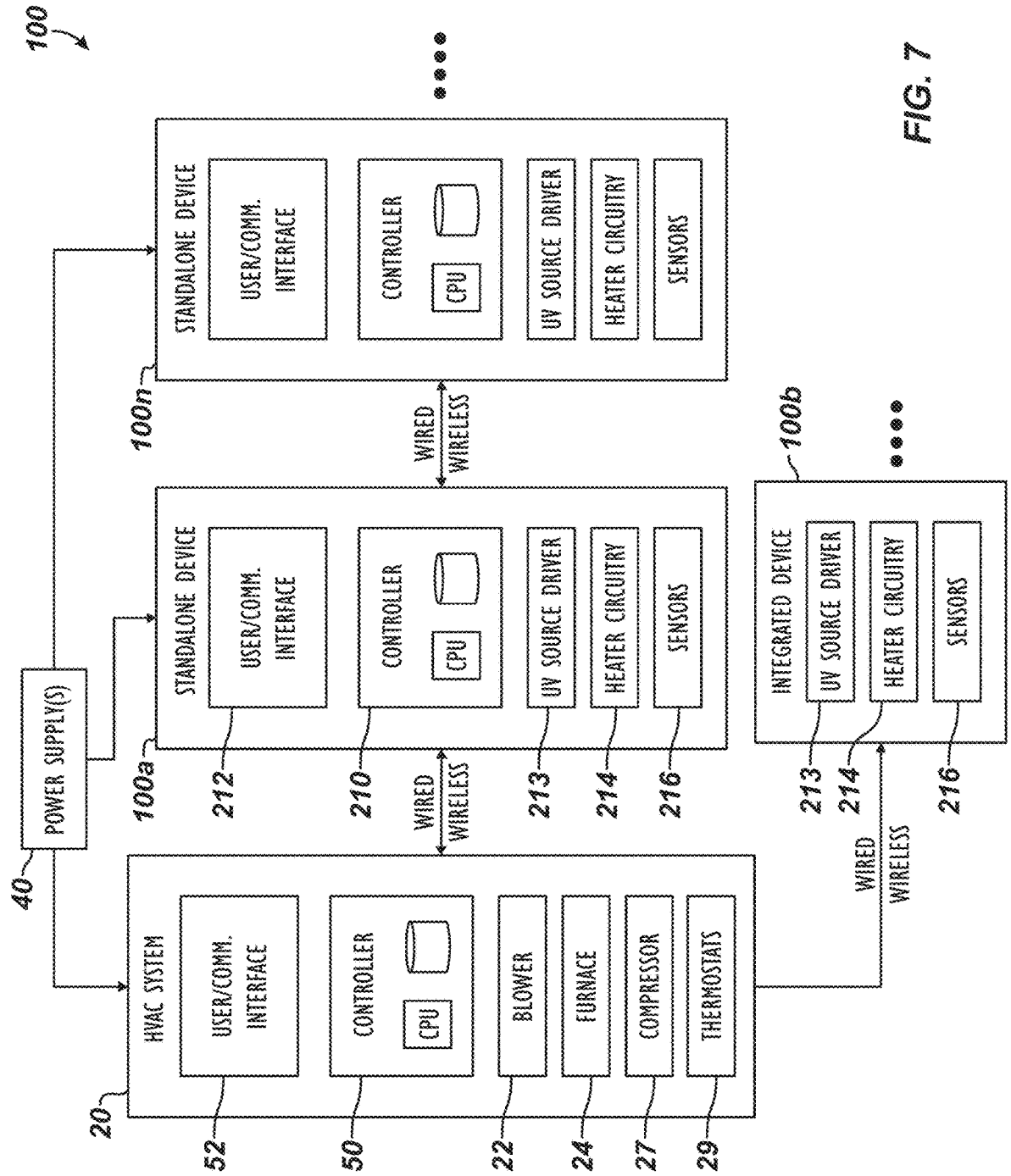
FIG. 7 illustrates a schematic arrangement of an air handling system having a number of purification devices.

As hinted to above, the disclosed purification device 100 can be used separately or in combination with an air handling system and other purification devices 100. FIG. 7 illustrates a schematic arrangement of an air handling system 20 having several purification devices 100a-n. As noted above, more than one purification device 100a-n can be used in a facility, and these devices 100a-n can have control configurations for remote or localized control.

For example, the air handling system 20 (e.g., HVAC system) can include its system controller 50 and can have user/communication interfaces 52. The system controller 50 includes a central processing unit and memory as typically found in environmental controllers. The user/communication interfaces 152 can include graphical user interfaces, control panels, wired communications, and wireless communications, such as typically found in environmental controllers. As before, the HVAC system 20 includes components, such as a blower 22, a furnace 24, a compressor 27, thermostats 29, and any other convention components.

The system controller 50 can communicate via wired or wireless communication with one or more stand-alone purification devices 110a-100n arranged in the facility. These stand-alone purification devices 110a-100n have local controllers 210 and user/communication interfaces 212. The local controller 210 includes a central processing unit and memory as typically found in environmental controllers. The user/communication interfaces 212 can include graphical user interfaces, control panels, wired communications, and wireless communications, such as typically found in environmental controllers. As before, the stand-alone devices 100a-100n include the disclosed purification components, such as the UV source driver 213, the heater circuitry 214, the sensors 216, etc.

As further shown, the system controller 50 can likewise communicate via wired or wireless communication with one or more integrated purification devices 110b arranged in the facility. These integrated devices 110b do not have local control and may be controlled directly by the system controller 50. As before, the integrated device 100b includes the disclosed purification components, such as the UV source driver 213, the heater circuitry 214, the sensors 216, etc.

Figure 8A:
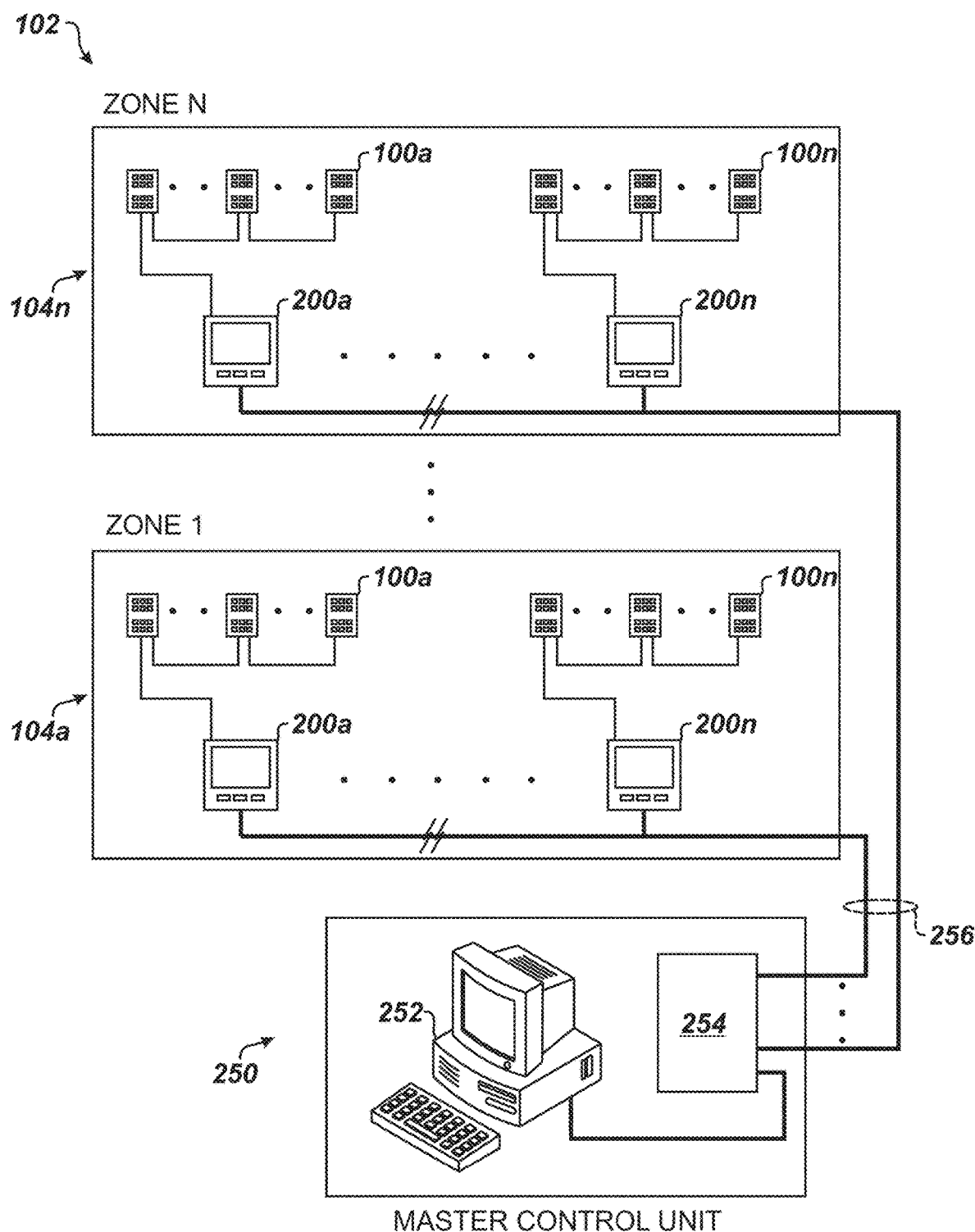
FIG. 8A illustrates a configuration having a number of purification devices subject to a master control unit.

Based on the above arrangement, it will be appreciated that the facility can be configured with multiple system components for different zones, rooms, areas, etc. of the facility. Briefly, FIG. 8A shows a master control unit 250 having a central processing unit 252 and communication interfaces 245 for communicating via wired and/or wireless communications 256 with multiple local controllers 200a-n in different zones 104a-n of a facility configuration 102. Each of the local controllers 200a-n can control one or more of the purification devices 100a-n in a given zone 104a-n.

Figure 8B:
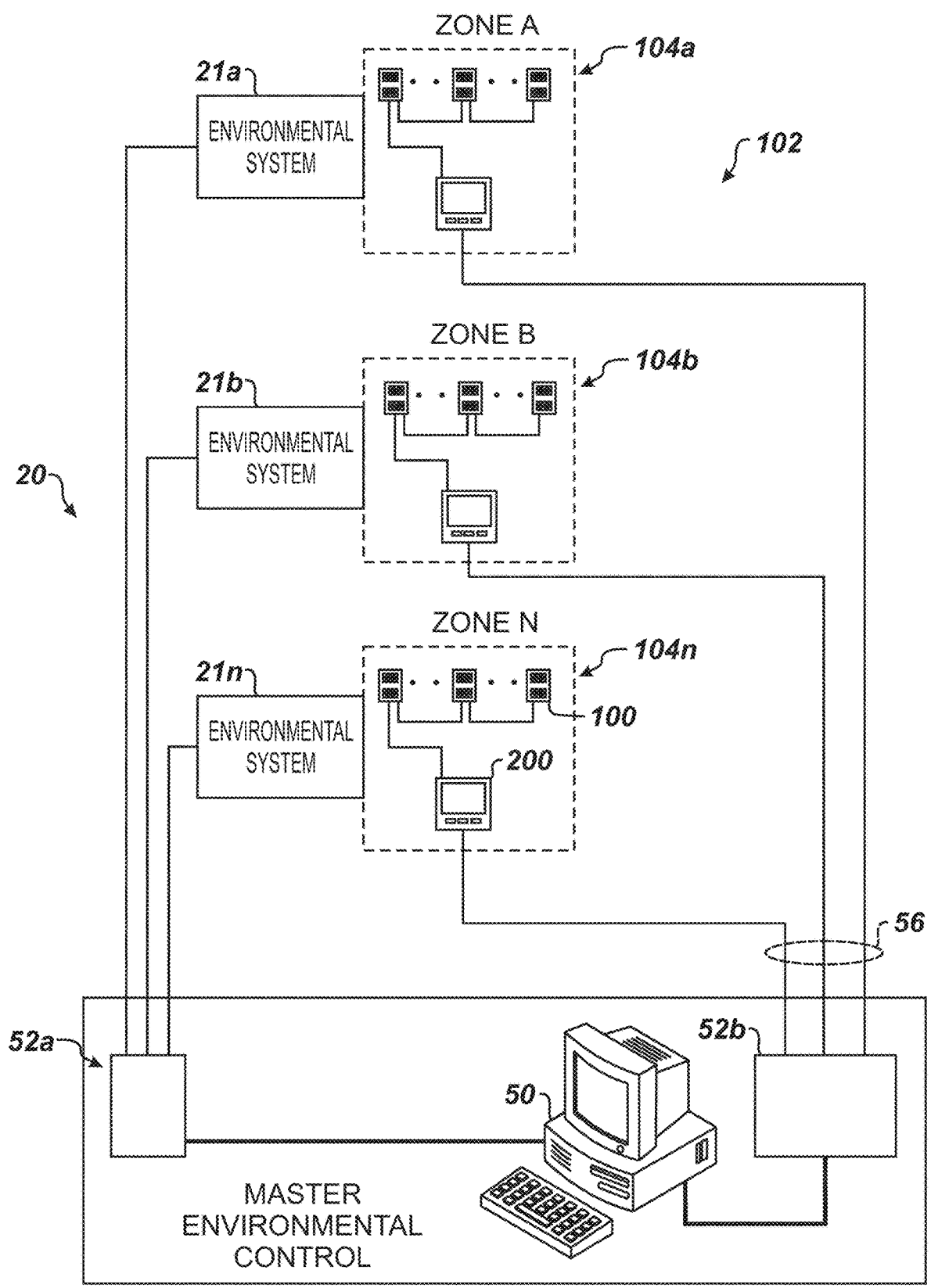
FIG. 8B illustrates another configuration having environmental components and several purification devices subject to a master environmental control.

As another brief example, FIG. 8B shows a master environmental control 50 having a central processing unit and communication interfaces 52a-b for communicating via wired and/or wireless communications 56 with multiple system components in the facility configuration 102. The master environment control 50 can communicate with local controllers 200a-n in different zones 104a-n of the facility configuration 102. Each of the local controllers 200a-n can control one or more of the purification devices 100a-n in a given zone 104a-n. Additionally, the master control 50 can communicate with local environmental systems 21a-n of the facility's air handling system 20. These local environmental systems 21a-n can be dedicated to different zones (e.g., floors, rooms, buildings, etc.) of a facility.

Figure 9A:
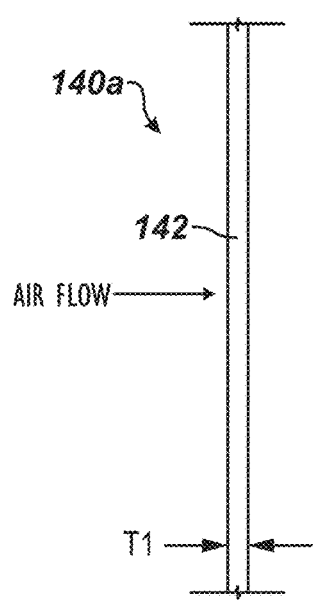
FIGS. 9A-9B illustrates side views of the permeable barrier for the disclosed heater in flat and corrugated configurations.
Figure 9B:
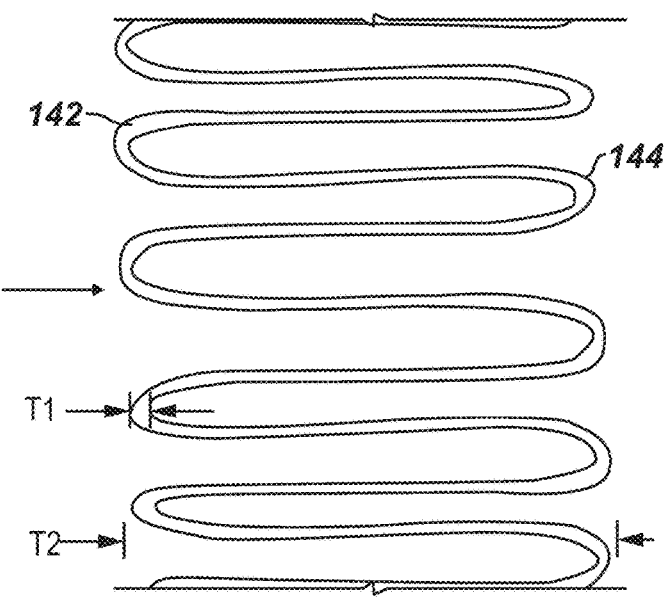

As noted previously, the permeable barrier 142 of the barrier heater 140 disclosed herein can have different layers and configurations. In FIG. 9A, a portion of a barrier heater 140a is shown with the permeable barrier 142 being flat and having a defined thickness T1. One or more such flat barriers 142 can be used adjacent one another in series to impede and interact with the impinging air flow. To increase surface area and the interaction, a portion of a barrier heater 140b is shown in FIG. 9B having folds, corrugations, or pleats 142 in the permeable barrier 142. The mesh material of the barrier 142 may have its original thickness T1, but the corrugated barrier heater 140b presents a thickness of T2 for the impinging air flow. One or more such corrugated barriers 142 can be used adjacent one another in series to impede and interact with the impinging air flow.

Considering the flexibility of Ni foam, the corrugated barrier heater 140b offers several advantages. First, the resistance of the Ni foam is much larger with the bends 144, which can help the barrier heater 140b when used with the residential voltage (110 V). Second, as illustrated in FIG. 9B, the bends 144 produce an effective distance T2 multiple times greater than the thickness T1 for interacting with the impinging air. The gaps between the bends 144 in the hot Ni foam create a high temperature that can be effective in damaging pathogens. It should be noted that the number of bends, the bending length, and the like can be easily controlled, and the longer the bending length, the higher the temperature can be achieved. Third, compared to the flat Ni foam with two main sides exposing to air, the bended Ni foam barrier 140b in FIG. 9B has a much smaller area exposed to the incoming and outgoing air, which will minimize the heat loss, so temperature of the barrier heater 140 can increase more rapidly and can reach to a much higher value at the same power consumption.

Figure 10A:
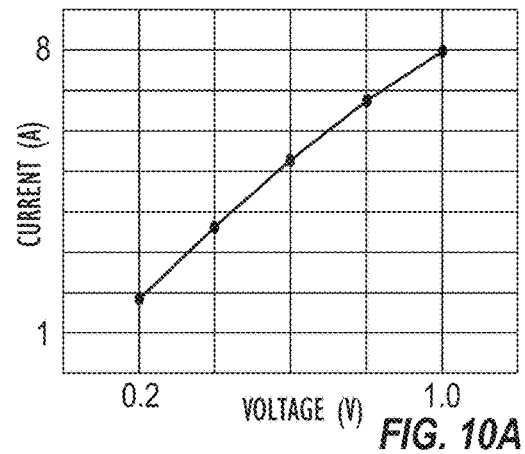
FIGS. 10A-10B illustrate graphs for the barrier heater having a flat configuration.
Figure 10B:
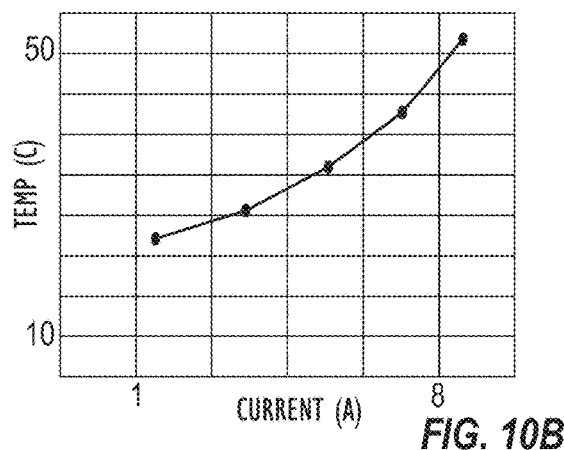
Figure 11A:
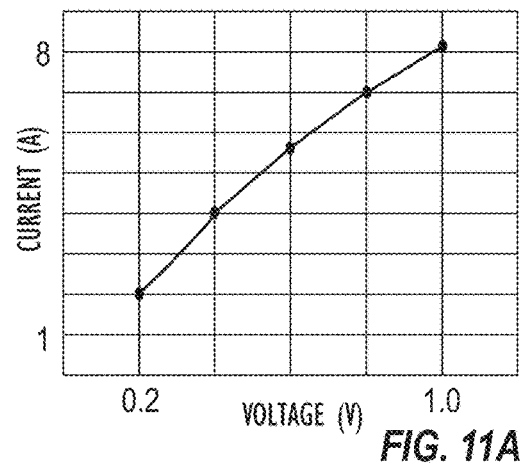
FIGS. 11A-11B illustrate graphs for the barrier heater having a corrugated configuration.
Figure 11B:
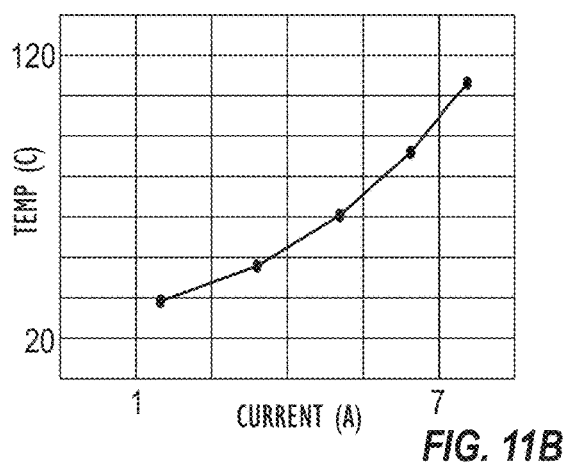

For example, FIG. 10A illustrates a graph of input voltage relative to the current produced for the barrier heater 140a having a flat Ni foam configuration, and FIG. 10B illustrates another graph of the current relative to a temperature level produced for the barrier heater 140a having the flat Ni foam configuration. Meanwhile, FIG. 11A illustrates a graph of input voltage relative to the current produced for the barrier heater 140b having corrugated Ni foam configuration, and FIG. 11B illustrates another graph of the current relative to a temperature level produced for the barrier heater 140b having the corrugated Ni foam configuration. As can be seen in FIGS. 10B and 11B, under the same voltage of 1.0 V, the temperature of the corrugated barrier heater 140b can be more than twice that of the flat barrier heater 140a.

As will be appreciated, various features of the disclosed purification device 100 with its UV light source 130 and barrier heater 140 can be configured to meet a particular implementation and to treat air for particular pathogens. Testing with actual pathogens requires careful controls, which has been conducted in laboratory environments.

As to the UV light source 130, the intensity, the active area, the wavelength, and other variables of the UV light from the source 130 can be configured to treat air for particular pathogens, and the variables are best determined by direct testing with actual pathogens in a controlled laboratory setting.

As to the barrier heater 140, the thickness, material, active surface area, permeability, corrugations, temperature, and other variables of the permeable barrier 142 from the barrier heater 140 can be configured to treat air for particular pathogens, and the variables are best determined by direct testing with actual pathogens in a controlled laboratory setting.

Previous studies with SARS-CoV and MERS-CoV have established that coronaviruses can be inactivated by heat. See e.g., See e.g., Leclerca, 2014; Darnell, 2004; Pastorino, 2020. Results of a preliminary study in a BSL3 facility showed SARS-CoV-2 is remarkably heat-resistant for an enveloped RNA virus. Only the 100° C. (212° F.) for 10 minutes protocol totally inactivated the virus.

Figure 12:
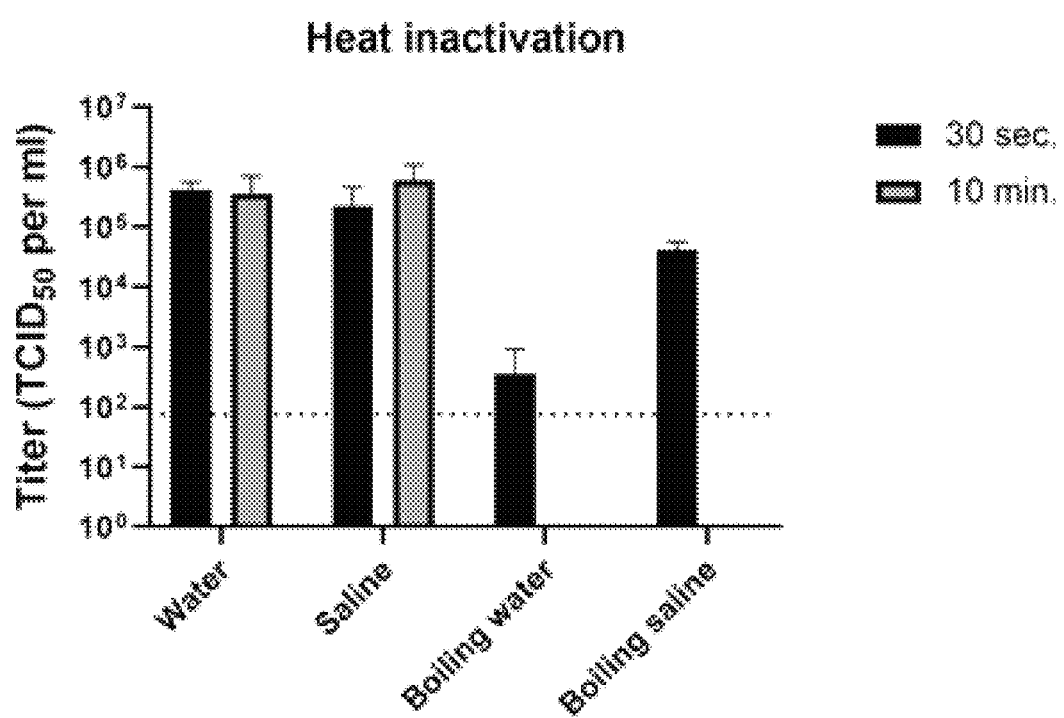
FIG. 12 illustrates a graph of exposure times and temperatures.

In particular, heat resistance of the Human SARS-CoV-2 strain (COVID-19) has been conducted in a BSL3 facility. The protocols for the study included using water and saline either at room temperature or at boiling temperature (FIG. 12). For the latter, 10 µL of SARS-CoV-2 was added to 90 µL of preheated water or saline at 100° C. (212° F.). These solutions were either incubated at 100° C. for either 30 seconds or 10 minutes whereas for the control arm incubation was carried out at room temperature.

After the incubation, 900 µL room-temperature media was added and titrated. The control arm of 10 min and 30 seconds incubation at room temperature remained ineffective in reducing the virus load. By contrast, the protocol 100° C.—30 seconds depicted a trend, but the exposure apparently was not long enough to effectively reduce the virus load, although the virus load in water was relatively lower compared to saline. Only the 100° C.-10 minute protocol for either water or saline was able to totally inactivate the virus (>5 $Log_{10}$ decrease).

The generated data confirms the virus to be remarkably heat-resistant for an enveloped RNA virus. Additional studies about the heat inactivation can illustrate curves for variable temperatures (50° C., 100° C., 150° C., 200° C., 250° C. & 300° C.) and exposure durations (1 sec, 5 sec, 15 sec, 30 sec, 1 min, 3 min, & 5 min), which can then be correlated to the expected heat damage caused by a barrier heater as disclosed herein, such as having a permeable Ni foam.

According to recent research, however, the heated filter of the disclosed barrier heater 140 can be used safely at high temperatures [(200-250° C.) (392-482° F.)] to kill COVID-19. In particular, research has been conducted at the Galveston National Lab/NIAID Biodefense Laboratory Network (Biosafety Level 4) and include findings of controlled experiments. The research has found COVID-19 to be vaporized in aerosolized air on contact with the specialized heated filter system of the present disclosure (i.e., the disclosed barrier heater 140). The results show a 100-fold decrease in active virus and a 100-percent kill rate of COVID-19 by the heated barrier heater 140. This research shows how COVID-19 can be eliminated from the air.

The disclosed purification device 100 can kill viruses and bacteria in the cycling air efficiently at high temperatures of about 250° C. (482° F.). As disclosed herein, the barrier heater 140, such as the nickel (Ni) foam, is low cost, electrically conductive, highly porous with random channels, and mechanically strong with good flexibility, which act as a good filter for sterilization and disinfection in an HVAC system or other environment. A bended Ni foam provides a structure with higher resistance and lower voltage and increases surface area for sterilization. A mechanical kill using temperature and a supercharged, high performance metal may be applied to the setting of COVID-19.

Other related research as disclosed herein has found that there is not a significant temperature increase in the air that passes through the disclosed heated filter given its high performance and design. Primary research of the filter and is conductivity was completed at the Superconductivity Center of Texas at The University of Houston. Research partners include Texas A&M University, Department of Engineering and Engineering Experiment Station and the University of Texas Medical Branch. As has been illustrated, the temperature of the barrier heater 140 of Ni foam increases very fast and can be heated to a high temperature with low wattage power. The air temperature decreases very fast after passing through the heated Ni foam of the barrier heater 140, even at temperatures over 100° C. (212° F.), the air temperature is room temperature at 4 cm away.

The foregoing description of preferred and other embodiments is not intended to limit or restrict the scope or applicability of the inventive concepts conceived of by the Applicants. It will be appreciated with the benefit of the present disclosure that features described above in accordance with any embodiment or aspect of the disclosed subject matter can be utilized, either alone or in combination, with any other described feature, in any other embodiment or aspect of the disclosed subject matter.

In exchange for disclosing the inventive concepts contained herein, the Applicants desire all patent rights afforded by the appended claims. Therefore, it is intended that the appended claims include all modifications and alterations to the full extent that they come within the scope of the following claims or the equivalents thereof.

What is claimed is:

1. An apparatus used with supplied power for treating air flow of an air handling system for a pathogen, the apparatus comprising:
   a frame having a plenum with an inlet and an outlet, the frame being configured to position in the air flow of the air handling system for passage of the air flow therethrough;
   a filter disposed across the plenum and comprising a first material, the filter being configured to filter the air flow therethrough up to a filtration threshold; and
   a heater disposed across the plenum and comprising a permeable barrier having a metal material, the permeable barrier of the heater being configured to allow the air flow therethrough up to a porosity threshold, the metal material of the permeable barrier of the heater connected in electrical communication to the supplied power, the permeable barrier having an active surface area being configured to interact with the pathogen and being heated by the supplied power to a surface temperature directed to at least damage the pathogen,
wherein the supplied power is not electrically connected to the filter such that the filter is not electrically connected to the supplied power and not heated while the heater is electrically connected to the supplied power and heated.

2. The apparatus of claim 1, wherein the permeable barrier of the heater comprises a mesh, a foam, a screen, or a tortuous media.

3. The apparatus of claim 1, wherein the metal material of the permeable barrier comprises nickel, nickel-based alloy, iron-based alloy, titanium, or steel alloy.

4. The apparatus of claim 1, wherein the first material of the filter comprises a metal material.

5. The apparatus of claim 1, further comprising an ultraviolet light source disposed in the plenum, the ultraviolet light source connected in electrical communication with the supplied power and configured to generate an active field of ultraviolet radiation in the plenum.

6. The apparatus of claim 5, further comprising a controller disposed in electrical communication with the ultraviolet light source and being configured to control (i) the heating of the permeable barrier by the supplied power and (ii) the radiation of the ultraviolet light source powered by the supplied power.

7. The apparatus of claim 6, wherein the controller is disposed in electrical communication with drive circuitry connected to the ultraviolet light source, the controller being configured to control the ultraviolet radiation of the ultraviolet light source with the drive circuitry powered by the supplied power.

8. The apparatus of claim 6, further comprising a light sensor disposed adjacent the ultraviolet light source and disposed in electrical communication with the controller, the light sensor being configured to measure the ultraviolet radiation associated with the ultraviolet light source.

9. The apparatus of claim 1, wherein to allow the air flow up to the porosity threshold, the permeable barrier of the heater is configured to impede the air flow therethrough up to an impedance threshold of 20 percent, giving the permeable barrier the porosity threshold of at least 80%.

10. The apparatus of claim 1, wherein the permeable barrier of the heater is heated to the surface temperature of at least greater than about 56° C. (133° F.).

11. The apparatus of claim 1, further comprising electrical insulation disposed between an edge of the permeable barrier and the frame.

12. The apparatus of claim 1, wherein the filter is disposed in the plenum toward the inlet, and the permeable barrier is disposed in the plenum toward the outlet.

13. The apparatus of claim 1, further comprising a controller disposed in electrical communication with the permeable barrier and being configured to control the heating of the permeable barrier by the supplied power.

14. The apparatus of claim 13, wherein the controller is disposed in electrical communication with heater circuitry connected to the permeable barrier, the controller configured to control the heating of the permeable barrier with the heater circuitry powered by the supplied power.

15. The apparatus of claim 14, further comprising a temperature sensor disposed adjacent the permeable barrier and disposed in electrical communication with the controller, the temperature sensor being configured to measure a temperature associated with the heating of the permeable barrier.

16. The apparatus of claim 13, wherein the controller comprises a communication interface disposed in communication with the air handling system and being configured to receive a signal indicative of the passage of the air flow through the apparatus, the controller configuring the control based on the signal received.

17. The apparatus of claim 13, further comprising a flow sensor disposed adjacent the plenum and disposed in electrical communication with the controller, the flow sensor being configured to measure the air flow passing through the plenum, the controller configuring the control based on the measured air flow.

18. The apparatus of claim 1, wherein the frame is configured to position in at least one of:
a return of the air handling system in a facility;
an intake of a furnace of the air handling system in a facility;
an outlet of the air handling system in a facility; and
a mixing chamber of the air handling system of a vehicle.

19. The apparatus of claim 1, the pathogen being a virus, wherein the active surface area of the permeable barrier is heated to the surface temperature of at least 200° C. directed to kill the virus.

20. A method for treating air flow of an air handling system for a pathogen, the method comprising:
positioning a frame in the air handling system for passage of the air flow therethrough;
filtering the air flow up to a filtration threshold through a filter disposed across a plenum of the frame between an inlet and outlet;
allowing the air flow up to a porosity threshold through a permeable barrier of a heater disposed across the plenum, the permeable barrier having a metal material and an active surface area, the active surface area being configured to interact with the pathogen; and
heating the active surface area of the permeable barrier of the heater to a surface temperature directed to at least damage the pathogen by supplying a voltage potential across the permeable barrier,
wherein no power is applied to the filter such that the filter is not electraically connected to the power and not heated while the heater is electrically connected to the power and heated.

21. The method of claim 20, further comprising producing an active field of ultraviolet radiation in the plenum by powering an ultraviolet light source disposed in the plenum.

22. The method of claim 20, wherein allowing the air flow up to the porosity threshold through the permeable barrier comprises impeding the air flow up to an impedance threshold of 20 percent, giving the permeable barrier the porosity threshold of at least 80%.

23. The apparatus of claim 1, further comprising carbon media disposed in the plenum.

24. The apparatus of claim 1, wherein the permeable barrier comprises one or more layers of porous foam having a thickness, the active surface area comprising a latticework of tortuous channels defined through the thickness of the porous foam.

25. The apparatus of claim 24, wherein the one or more layers are corrugated.

26. The apparatus of claim 1, further comprising a controller being configured to control heating of the active surface area of the permeable barrier intermittently, when the air flow is passing through the permeable barrier, and/or when the air flow is not passing through the permeable barrier.

27. The apparatus of claim 1, wherein the active surface area heated to the surface temperature and the porosity threshold of the permeable barrier are configured to produce heating that is localized and is dissipated in the air flow downstream thereof.

28. The apparatus of claim 1, wherein the filter is a high-efficiency particulate air filter, the filter is configured to filter the air flow therethrough up to the filtration threshold that stops 99.9 percent of particles with a diameter of a 0.3 microns or greater resulting in a filtered air flow.

29. An apparatus for treating air flow of an air handling system for a pathogen, the apparatus comprising:

a frame having a plenum with an inlet and an outlet, the frame being configured to position in the air flow of the air handling system for passage of the air flow therethrough;

a filter disposed across the plenum proximate the inlet of the frame, the filter being configured to filter the air flow therethrough up to a filtration threshold resulting in a filtered airflow;

a heater disposed across the plenum proximate the outlet of the frame, the heater comprising a permeable barrier configured to impede the filtered air flow therethrough up to an impedance threshold, the permeable barrier having an active surface area being configured to interact with the pathogen;

insulation separating the permeable barrier from the frame; and a supplied power electrically connected to the permeable barrier, wherein the permeable barrier is heated by the supplied power to a surface temperature directed to kill the pathogen, and wherein the supplied power is not electrically connected to the filter such that the filter is not electrically connected to the supplied power and not heated while the heater is electrically connected to the supplied power and heated.

30. The apparatus of claim 29, wherein the filter is a high-efficiency particulate air filter, the filter is configured to filter the air flow therethrough up to the filtration threshold that stops 99.9 percent of particles with a diameter of a 0.3 microns or greater resulting in a filtered air flow.

31. The apparatus of claim 29, wherein the filter comprises a first metal material and the permeable barrier comprises a second metal material that is different than the first metal material of the filter.

32. The apparatus of claim 31, wherein the first metal material is aluminum or stainless steel.

33. The apparatus of claim 31, wherein the second metal material is nickel, nickel-based alloy, iron-based alloy, titanium, or steel alloy.

* * * * *